United States Patent
Haidukewych et al.

(10) Patent No.: US 12,364,608 B2
(45) Date of Patent: *Jul. 22, 2025

(54) INTERCONNECTED IMPLANTS AND METHODS

(71) Applicant: REVISION TECHNOLOGIES LLC, Orlando, FL (US)

(72) Inventors: George J. Haidukewych, Orlando, FL (US); Daniel F. Justin, Orlando, FL (US)

(73) Assignee: REVISION TECHNOLOGIES LLC, Orlando, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/967,399

(22) Filed: Dec. 3, 2024

(65) Prior Publication Data

US 2025/0090333 A1    Mar. 20, 2025

Related U.S. Application Data

(63) Continuation of application No. 17/183,246, filed on Feb. 23, 2021, now Pat. No. 12,156,816, which is a continuation of application No. 16/442,429, filed on Jun. 14, 2019, now Pat. No. 10,945,850.

(60) Provisional application No. 62/750,781, filed on Oct. 25, 2018.

(51) Int. Cl.
*A61F 2/36* (2006.01)
*A61B 17/80* (2006.01)
*A61F 2/46* (2006.01)

(52) U.S. Cl.
CPC ........ *A61F 2/3609* (2013.01); *A61B 17/8061* (2013.01); *A61F 2/3601* (2013.01); *A61F 2/367* (2013.01); *A61F 2002/3611* (2013.01); *A61F 2002/3625* (2013.01); *A61F 2/4603* (2013.01)

(58) Field of Classification Search
CPC ...... A61F 2/3609; A61F 2/3601; A61F 2/367; A61F 2002/3611; A61F 2002/3625; A61B 17/8061
See application file for complete search history.

(56) References Cited

U.S. PATENT DOCUMENTS

| | | | | |
|---|---|---|---|---|
| 3,939,498 | A * | 2/1976 | Lee | A61F 2/30739 623/23.27 |
| 4,858,602 | A * | 8/1989 | Seidel | A61B 17/7241 606/62 |
| 5,356,410 | A * | 10/1994 | Pennig | A61B 17/746 606/62 |

(Continued)

*Primary Examiner* — Alvin J Stewart
(74) *Attorney, Agent, or Firm* — David Meibos; Maywood IP Law

(57) ABSTRACT

An apparatus, system, and method may be used to replace a natural or artificial articular surface of a joint, and to repair a bone that is associated with the joint. In some embodiments, the apparatus, system, and method may include a joint replacement prosthesis with a prosthetic articular surface, a support structure securable to the bone, and a first attachment interface. The system may also include a bone plate with a bone engagement surface securable to the bone on either side of a fracture formed in the bone, or a damaged area of the bone. The bone plate may include a second attachment interface that is attachable to the first attachment interface of the joint replacement prosthesis in order to couple the bone plate to the joint replacement prosthesis.

23 Claims, 19 Drawing Sheets

(56) References Cited

U.S. PATENT DOCUMENTS

| | | | | |
|---|---|---|---|---|
| 7,632,272 | B2* | 12/2009 | Munro | A61B 17/744 606/67 |
| 8,118,868 | B2* | 2/2012 | May | A61F 2/367 623/13.14 |
| 8,147,493 | B2* | 4/2012 | Dutoit | A61B 17/8085 606/65 |
| 8,906,109 | B2* | 12/2014 | Smith | A61F 2/34 623/22.46 |
| 9,398,928 | B2* | 7/2016 | Chavarria | A61F 2/40 |
| 9,463,054 | B2* | 10/2016 | Mueckter | A61B 17/7241 |
| 10,945,850 | B2* | 3/2021 | Haidukewych | A61B 17/7233 |
| 11,413,153 | B2* | 8/2022 | Zhu | A61F 2/3672 |
| 12,156,816 | B2* | 12/2024 | Haidukewych | A61F 2/367 |
| 2004/0236337 | A1* | 11/2004 | Deloge | A61B 17/74 606/74 |
| 2008/0177393 | A1* | 7/2008 | Grant | A61F 2/40 623/20.11 |
| 2009/0164026 | A1* | 6/2009 | Mikami | A61F 2/30739 623/23.23 |
| 2011/0130840 | A1* | 6/2011 | Oskouei | A61F 2/36 623/18.11 |
| 2011/0218636 | A1* | 9/2011 | Smith | A61B 17/1753 623/20.35 |
| 2011/0218641 | A1* | 9/2011 | Smith | A61F 2/30734 623/22.42 |
| 2013/0261622 | A1* | 10/2013 | Bonjour | A61B 17/746 606/64 |
| 2014/0107711 | A1* | 4/2014 | Norris | A61F 2/30739 606/291 |
| 2015/0182266 | A1* | 7/2015 | Jakob | A61B 17/74 606/280 |
| 2019/0117412 | A1* | 4/2019 | Zimmerman | A61B 17/1668 |
| 2020/0129297 | A1* | 4/2020 | Haidukewych | A61B 17/744 |

* cited by examiner

INTERCONNECTED IMPLANTS AND METHODS

CROSS-REFERENCE TO RELATED APPLICATIONS

This application is a continuation of U.S. patent application Ser. No. 17/183,246 filed on Feb. 23, 2021, which issued on Dec. 3, 2024 as U.S. Pat. No. 12,156,816, which is a continuation of U.S. patent application Ser. No. 16/442,429 filed on Jun. 14, 2019, entitled "INTERCONNECTED IMPLANTS AND METHODS", which issued on Mar. 16, 2021 as U.S. Pat. No. 10,945,850, which claims the benefit of U.S. Provisional Patent Application No. 62/750,781 filed on Oct. 25, 2018, entitled "INTERCONNECTED HIP IMPLANTS AND METHODS", the disclosures of which are incorporated herein by reference in their entirety.

TECHNICAL FIELD

The present disclosure relates to surgical devices, systems, and methods. More specifically, the present disclosure relates to interconnected joint prosthesis implants and bone plates for replacing an articulating surface of a joint, as well as for repairing one or more bones associated with the joint.

BACKGROUND

Joint arthroplasty procedures are surgical procedures in which one or more articulating surfaces of a joint are replaced with prosthetic articulating surfaces. Such procedures are becoming increasingly commonplace.

Some joint replacements are necessitated by trauma. In such cases, it may be desirable to repair one of the bones associated with, or adjacent to, the joint as part of the same surgical procedure in which a partial or full joint replacement is carried out. Furthermore, in some cases, a previous joint arthroplasty procedure may need to be revised, for example, by removing one or more previously implanted components and inserting new components. Sometimes in the context of revision, repair of a bone fracture is needed, along with the partial or full joint replacement.

In one non-limiting example, the greater trochanter of a femur may receive significant loading, particularly after a hip replacement is carried out that replaces the ball of the femur with a prosthetic ball. Accordingly, in this example, there may be a need to repair a fracture of the greater trochanter at the time the joint is first replaced, or at the time of revision of the first joint replacement. Known joint replacement and fracture repair systems often lack sufficient implant stability and interoperability.

SUMMARY

A system may be used to replace a natural or artificial articular surface of a joint, and to repair a bone that is associated with the joint. The joint may be a hip or shoulder joint, and the bone may be a femur or humerus, as two non-limiting examples.

In one embodiment, the system may include a joint replacement prosthesis with a prosthetic articular surface, a support structure securable to the bone, and a first attachment interface. The system may also include a bone plate with a bone engagement surface securable to the bone on either side of a fracture formed in the bone, and a second attachment interface that is attachable to the first attachment interface of the joint replacement prosthesis in order to couple the bone plate to the joint replacement prosthesis.

In various embodiments of the system, the joint replacement prosthesis may include at least one of: a femoral joint replacement prosthesis; a tibial joint replacement prosthesis; a fibular joint replacement prosthesis; a humeral joint replacement prosthesis; a clavicle joint replacement prosthesis; a radial joint replacement prosthesis; an ulnar joint replacement prosthesis; a digital joint replacement prosthesis; and an intramedullary nail.

The system may also include a fastening system configured to engage the second attachment interface with the first attachment interface and couple the bone plate to the joint replacement prosthesis. In at least some embodiments, the fastening system may include a bolt and a washer. In at least some embodiments, the second attachment interface of the bone plate may be attachable to the first attachment interface of the joint replacement prosthesis at any of a first plurality of relative orientations about a first axis, and at any of a second plurality of relative orientations about a second axis, wherein the second axis is orthogonal to the first axis. The first attachment interface may include a dome having a first generally semispherical shape with a first radius. The second attachment interface may include a recess having a second generally semispherical shape with a second radius, wherein the second generally semispherical shape of the recess is complementary to the first generally semispherical shape of the dome. The first generally semispherical shape and the second generally semispherical shape may have substantially the same radius.

The bone plate of the system may further include at least one arm extending proximate the second attachment interface, at least one central expanse coupled to the at least one arm, and at least one bone engagement feature coupled to the at least one central expanse. One or more of the at least one arm, the at least one central expanse, and the at least one bone engagement feature may be bendable, such that the one or more of the at least one arm, the at least one central expanse, and the at least one bone engagement feature can be shaped to conform to at least one surface of the bone.

The at least one central expanse of the bone plate of the system may further include an aperture formed in the at least one central expanse in order to facilitate flexure of the at least one central expanse so that the at least one central expanse can be shaped to conform to the at least one surface of the bone. The at least one central expanse may be securable to the bone on a first side of the fracture that is formed in the bone, via a first bone engagement feature, and a second side of the fracture that is formed in the bone, via a second bone engagement feature.

In at least one embodiment of the system, the at least one arm may be further configured to allow the at least one central expanse to translate with respect to the at least one arm to in order to compress the at least one central expanse against the at least one surface of the bone.

In at least one embodiment of the system, the first attachment interface and the second attachment interface may be further configured to allow for rotational adjustment of the bone plate with respect to the joint replacement prosthesis.

In a particular embodiment, an apparatus for replacing a natural or artificial articular surface of a hip joint and for repairing a greater trochanter of a femur associated with the hip joint may include a hip prosthesis with a neck that is securable to the femur associated with the hip joint, an arm coupled to the neck, a prosthetic ball comprising an articular surface, wherein the prosthetic ball is couplable to the arm of the hip prosthesis, and a first attachment interface formed on a superior surface of the hip prosthesis. The apparatus may further include a bone plate with a bone engagement surface that is securable to the greater trochanter of the femur on either side of a fracture formed in the greater trochanter of the femur, and a second attachment interface that is attachable to the first attachment interface of the hip prosthesis in order to couple the bone plate to the hip prosthesis.

The apparatus may further include a fastening system configured to engage the second attachment interface with the first attachment interface and couple the bone plate to the hip prosthesis. In at least one embodiment, the fastening system may include a bolt and a washer. In some embodiments, the second attachment interface of the bone plate may be attachable to the first attachment interface of the hip prosthesis at any of a first plurality of relative orientations about a first axis, and at any of a second plurality of relative orientations about a second axis, wherein the second axis is orthogonal to the first axis. The first attachment interface may include a dome having a first generally semispherical shape with a first radius. The second attachment interface may include a recess having a second generally semispherical shape with a second radius, wherein the second generally semispherical shape of the recess is complementary to the first generally semispherical shape of the dome. The first generally semispherical shape and the second generally semispherical shape may have substantially the same radius.

The bone plate of the apparatus may further include at least one arm extending proximate the second attachment interface, at least one central expanse coupled to the at least one arm, and at least one bone engagement feature coupled to the at least one central expanse. One or more of the at least one arm, the at least one central expanse, and the at least one bone engagement feature may be bendable, such that the one or more of the at least one arm, the at least one central expanse, and the at least one bone engagement feature can be shaped to conform to at least one surface of the greater trochanter of the femur.

The at least one central expanse of the bone plate of the apparatus may further include an aperture formed in the at least one central expanse in order to facilitate flexure of the at least one central expanse so that the at least one central expanse can be shaped to conform to the at least one surface of the greater trochanter of the femur. The at least one central expanse may be securable to the bone on a first side of the fracture that is formed in the greater trochanter of the femur, via a first bone engagement feature, and a second side of the fracture that is formed in the greater trochanter of the femur, via a second bone engagement feature.

In at least one embodiment of the apparatus, the at least one arm may be further configured to allow the at least one central expanse to translate with respect to the at least one arm to in order to compress the at least one central expanse against the at least one surface of the greater trochanter of the femur.

In at least one embodiment of the apparatus, the first attachment interface and the second attachment interface may be further configured to allow for rotational adjustment of the bone plate with respect to the hip prosthesis. In certain embodiments, the first attachment interface and the second attachment interface may be configured to allow for discrete rotational adjustments of the bone plate with respect to the hip prosthesis from among a plurality of different discrete rotational positions. In other embodiments, the first attachment interface and the second attachment interface may be configured to allow for an infinite number of rotational adjustment positions between the bone plate and the hip prosthesis.

According to another embodiment, a method of replacing a natural or artificial articular surface of a joint and repairing a bone associated with the joint may include coupling a joint replacement prosthesis to the bone associated with the joint, replacing an articular surface of the joint with a prosthetic articular surface of the joint replacement prosthesis that is coupled to the bone associated with the joint, coupling a bone plate to the joint replacement prosthesis, and securing the bone plate proximate a damaged area of the bone to facilitate repair of the damaged area of the bone associated with the joint.

The method may also include bending at least one of: an arm of the bone plate, a central expanse of the bone plate, and a bone engagement feature of the bone plate, in order to shape the bone plate to conform to at least one surface of the bone associated with the joint.

The method may also include translating the central expanse of the bone plate with respect to the arm of the bone plate and compressing the central expanse of the bone plate against at least one surface of the bone associated with the joint prior to securing the bone plate to the bone associated with the joint.

The method may also include rotating the bone plate to a desired position with respect to the joint replacement prosthesis prior to securing the bone plate to the bone associated with the joint.

In various embodiments of the method, the joint replacement prosthesis may include at least one of: a femoral joint replacement prosthesis; a tibial joint replacement prosthesis; a fibular joint replacement prosthesis; a humeral joint replacement prosthesis; a clavicle joint replacement prosthesis; a radial joint replacement prosthesis; an ulnar joint replacement prosthesis; a digital joint replacement prosthesis; and an intramedullary nail.

These and other features and advantages of the present disclosure will become more fully apparent from the following description and appended claims, or may be learned by the practice of the systems and methods set forth hereinafter.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the present disclosure will be described with additional specificity and detail through use of the accompanying drawings in which:

It will be understood that the Figures are for purposes of illustrating the concepts of the present disclosure and may not be drawn to scale. Furthermore, the Figures illustrate exemplary embodiments and do not represent limitations to the scope of the present disclosure.

DETAILED DESCRIPTION

Exemplary embodiments of the present disclosure will be best understood by reference to the Figures, wherein like parts are designated by like numerals throughout. It will be readily understood that the components of the present disclosure, as generally described and illustrated in the Figures herein, could be arranged and designed in a wide variety of different configurations. Thus, the following more detailed description of the embodiments of the apparatus, systems, and methods, as represented in the Figures, is not intended to limit the scope of the present disclosure, as claimed in this or any other application claiming priority to this application, but is merely representative of exemplary embodiments of the present disclosure.

Standard medical directions, planes of reference, and descriptive terminology are employed in this specification. For example, anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. A sagittal plane divides a body into right and left portions. A midsagittal plane divides the body into bilaterally symmetric right and left halves. A coronal plane divides a body into anterior and posterior portions. A transverse plane divides a body into superior and inferior portions. These descriptive terms may be applied to an animate or inanimate body.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Figure 1A:
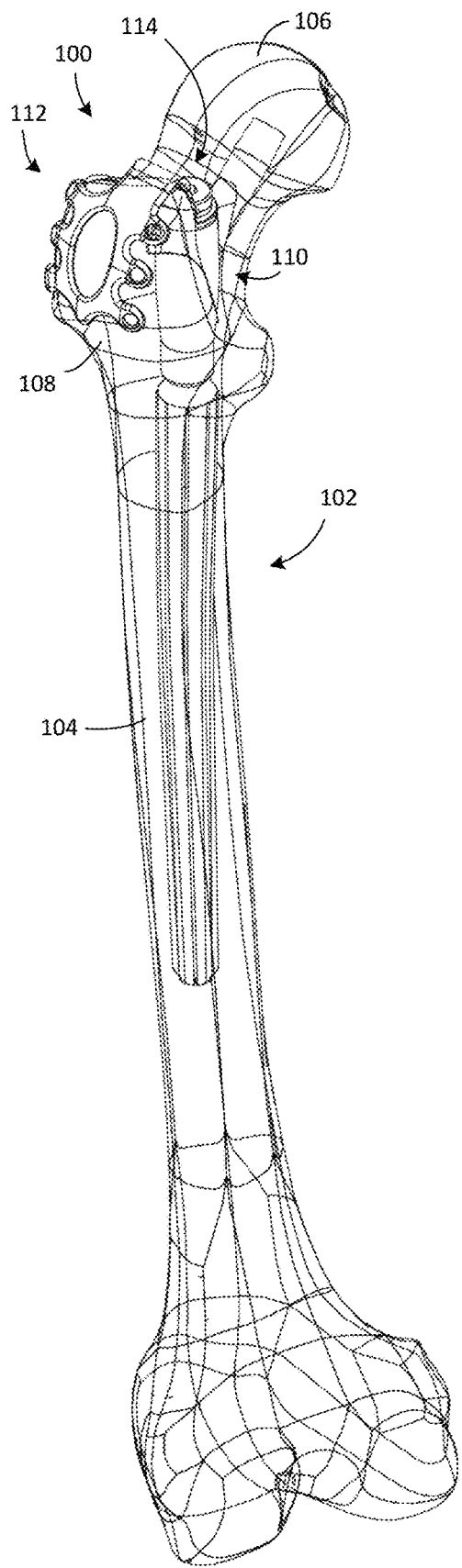
FIG. 1A is a perspective view of a hip implant system 100 implanted in a femur, according to an embodiment of the present disclosure.
Figure 1B:
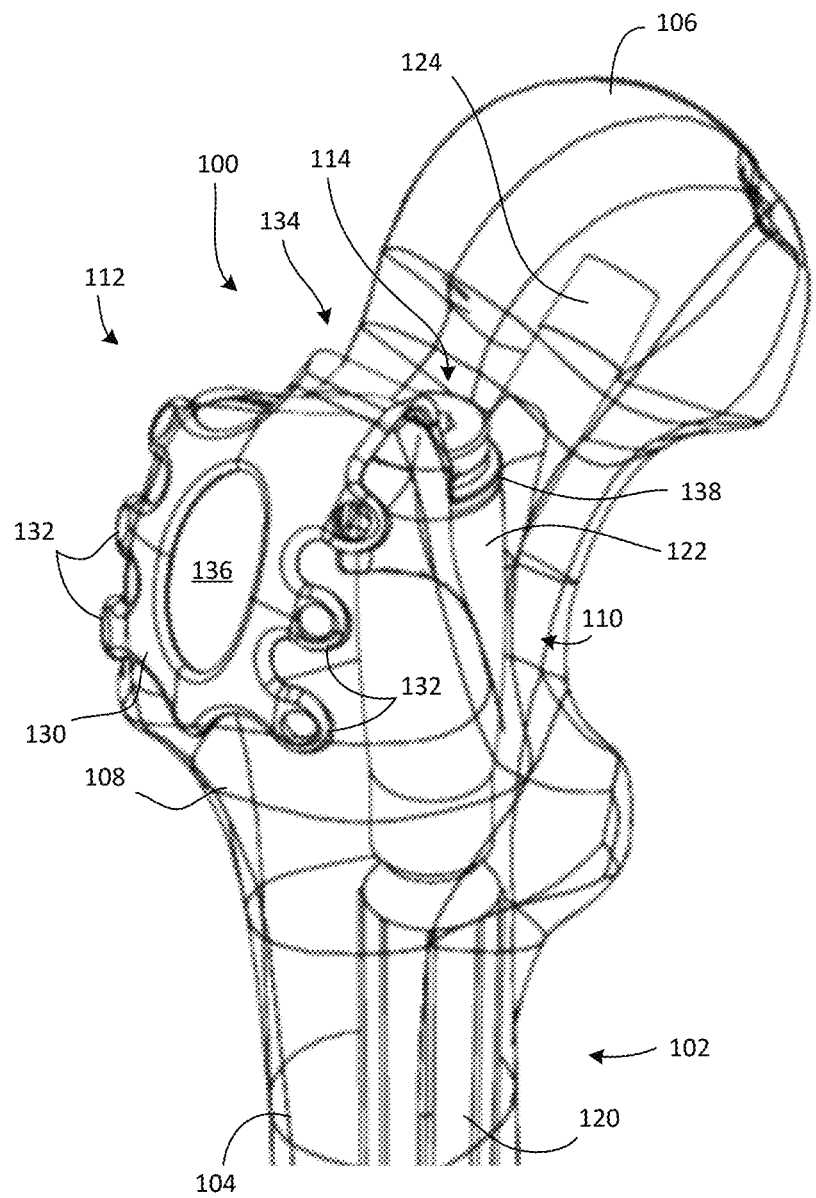
FIG. 1B is a close up perspective view of the hip implant system 100 of FIG. 1A.
Figure 2A:
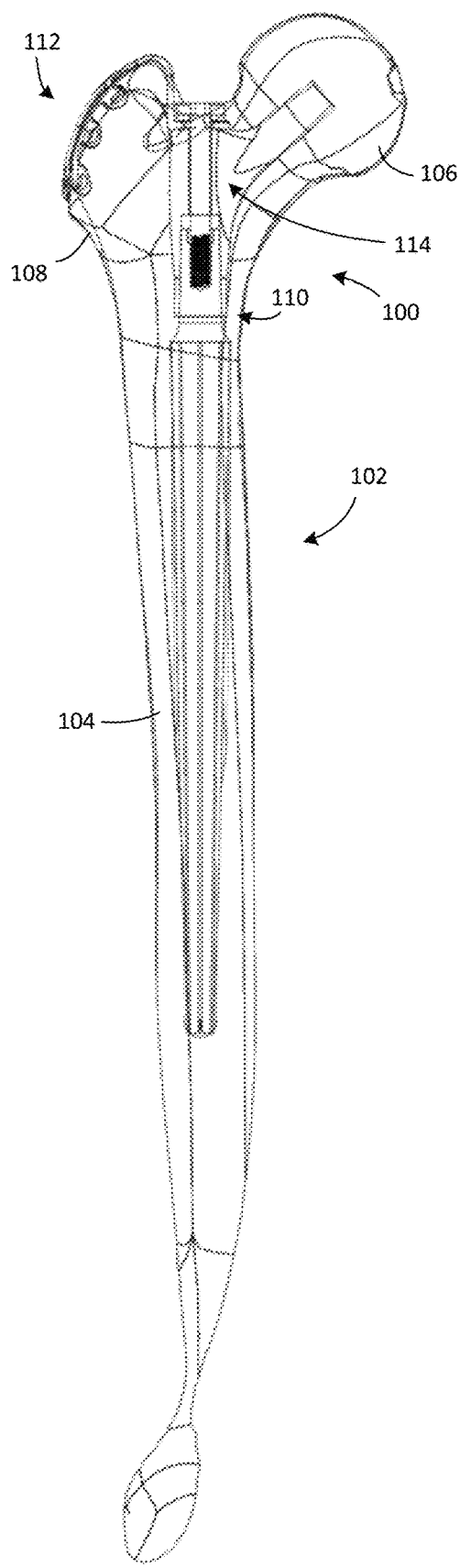
FIG. 2A is a front elevation, section view of the hip implant system 100 shown in FIG. 1A.
Figure 2B:
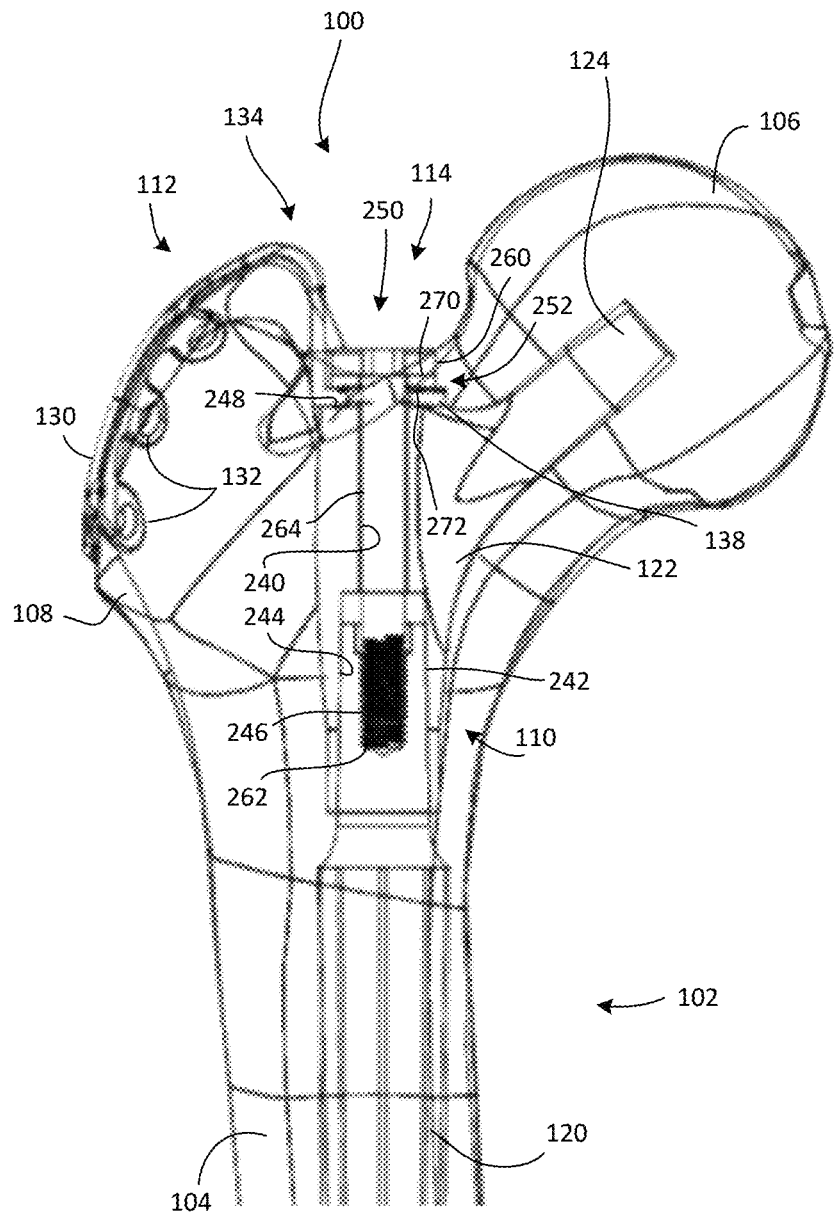
FIG. 2B is a close up view of the hip implant system 100 shown in FIG. 2A.
Figure 3:
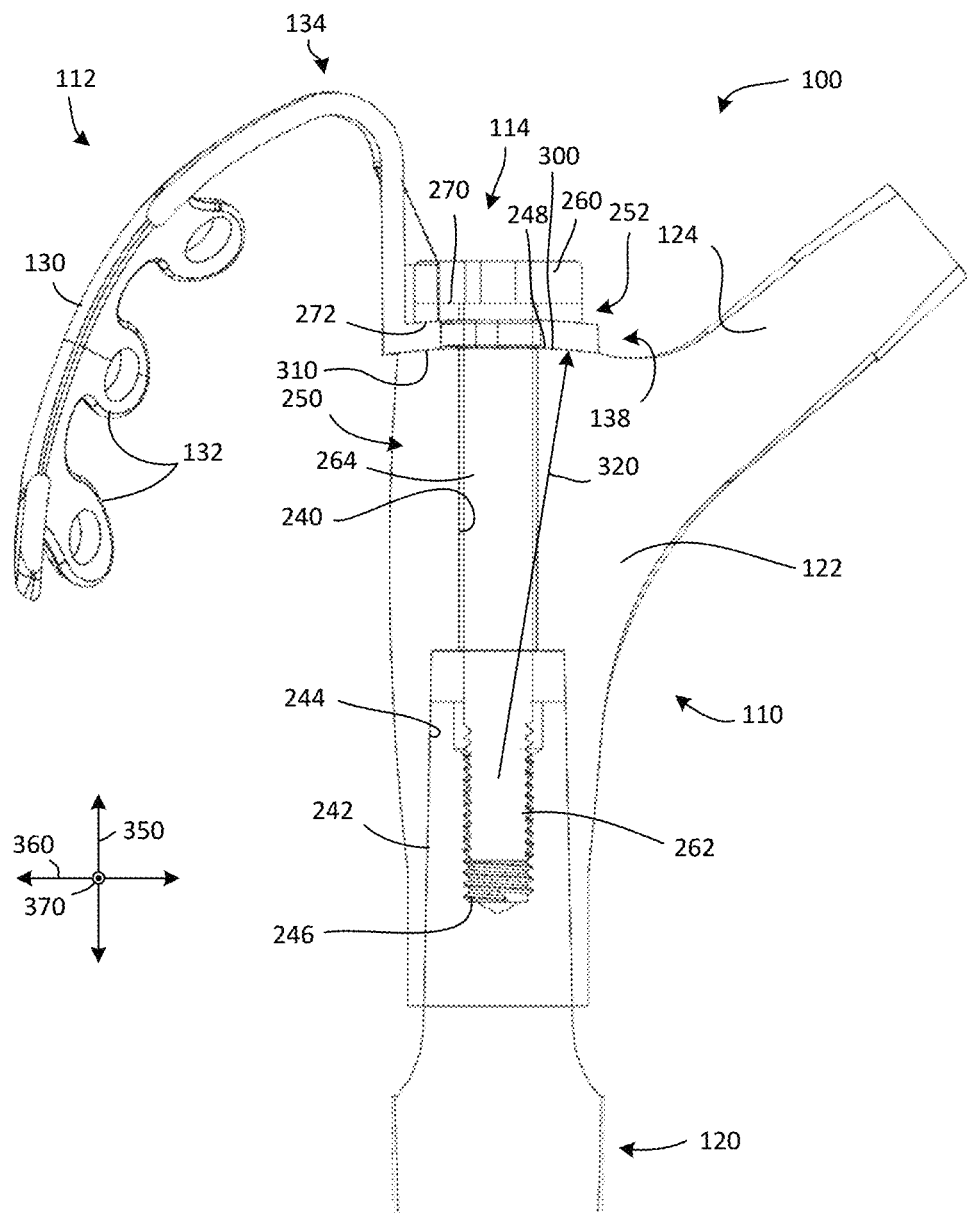
FIG. 3 shows the hip implant system 100 shown of FIG. 2A (without the femur), illustrating the fastening system 114 and first and second attachment interfaces 300, 310 of the hip implant system 100.

FIGS. 1A-3 illustrate various views of a hip implant system 100, according to one embodiment of the present disclosure. Specifically, FIG. 1A is a perspective view of the hip implant system 100 implanted in a femur 102; FIG. 1B is a close up perspective view of the hip implant system 100 of FIG. 1A; FIG. 2A is a front elevation, section view of the hip implant system 100 of FIG. 1A; FIG. 2B is a close up view of the hip implant system 100 shown in FIG. 2A; and FIG. 3 shows the hip implant system 100 of FIG. 2A without the femur 102, to illustrate a fastening system 114 and the first and second attachment interfaces 300, 310 of the hip implant system 100.

As shown in FIGS. 1A-2B, the femur 102 may have a body 104, a ball 106, and a greater trochanter 108. The hip implant system 100 may be designed to replace one or more natural articulating surfaces of the ball 106, and may also be designed to repair and/or strengthen the greater trochanter 108. Thus, the hip implant system 100 may include a hip prosthesis 110 and a bone plate 112, which may be secured together via a fastening system 114.

The hip prosthesis 110 may have the configuration and components of any hip implant known in the art. The hip prosthesis 110 may be designed as a revision implant that replaces a prior hip prosthesis (not shown) that is no longer suitable due to wear, loosening, infection, and/or for other reasons. The hip prosthesis 110 may have a stem 120, a neck 122, and an arm 124. The stem 120 may reside within the intramedullary canal of the femur 102, specifically within the body 104 of the femur 102, and may thus provide a support structure to support the hip prosthesis 110 relative to the femur 102. The neck 122 may optionally also reside within the intramedullary canal of the femur 102, proximal to the stem 120. The stem 120 and the neck 122 may optionally be separate pieces, allowing for stems with different sizes and/or lengths to be used in combination with one or more necks.

As shown, the neck 122 may be formed as a single piece with the arm 124. The arm 124 may have a Morse taper or other interface to which a prosthetic ball (not shown) may be attached. The prosthetic ball may replace the ball 106 of the femur 102, which may be removed, or in the case of a revision surgery, may already have been removed and replaced with a previous prosthetic ball. Modularity between the prosthetic ball and the arm 124 may permit a variety of different prosthetic balls and arms to be used interchangeably with each other. Thus, the surgeon may, in some embodiments, make up the hip prosthesis 110 by selecting the stem 120 from a plurality of stems, selecting the neck 122 and the arm 124 from a plurality of neck and arm components, and selecting the prosthetic ball from a plurality of prosthetic balls.

The bone plate 112 may be designed to remedy a fracture or weakness (not shown) in the greater trochanter 108. The bone plate 112 may have the shape and features of any bone plate known in the art. The bone plate 112 may have at least one bone engagement feature 132, at least one central expanse 130, and/or at least one arm 134.

The central expanse 130 is shown with a shape that generally conforms to that of the greater trochanter 108, with an oval aperture 136 that facilitates flexure of the central expanse 130 to enable the central expanse 130 to bend into greater conformity with the surface of the greater trochanter 108, as the central expanse 130 is installed. The oval aperture 136 may also reduce the weight of the central expanse 130.

The bone engagement features 132 may have any configuration known in the art. As embodied in FIGS. 1A-3, the bone engagement features 132 may be eyelets through which fasteners, such as bone screws (not shown), may be inserted to secure the periphery of the central expanse 130 to the greater trochanter 108. In other embodiments, alternative bone fastening methods, such as pins or spikes (not shown), may be used to secure the bone plate 112 to the greater trochanter 108 in other ways.

The arm 134 may have a gooseneck shape that extends over the superior aspect of the greater trochanter 108, and then distally toward the proximal end of the intramedullary canal of the femur 102, where the proximal end of the neck 122 is located. The arm 134 may terminate in a ring 138 that may be used to secure the arm 134 of the bone plate 112 to the neck 122 of the hip prosthesis 110. Like the central expanse 130, the arm 134 may also be thin enough to be somewhat malleable, such that the arm 134 may be bent into closer conformity with the superior end of the femur 102 during implantation.

The bone plate 112 may also be a modular component of the hip implant system 100. In some examples, the bone plate 112 may be selected from a number of differently-sized and/or differently-shaped bone plates. As a variety of fractures may occur in the greater trochanter 108, such bone plates may have different configurations, each of which may address a specific fracture type and/or fracture severity.

The hip prosthesis 110 and the bone plate 112 may be secured together through use of the fastening system 114. In some embodiments, the fastening system 114 may secure the bone plate 112 to the hip prosthesis 110 at any of a plurality of relative orientations. Thus, the fastening system 114 may be operable to secure the hip prosthesis 110 to the bone plate 112 with a variety of bone geometries. The fastening system 114 may further secure two or more components of the hip prosthesis 110 together. As embodied in FIGS. 1A-3, the fastening system 114 may secure the stem 120 to the neck 122, in addition to securing the hip prosthesis 110 to the bone plate 112.

As shown in FIGS. 2B and 3, the neck 122 of the hip prosthesis 110 may have a bore 240 that extends the entire length through the neck 122. The stem 120 of the hip prosthesis 110 may have a tapered extension 242 that is inserted into a counterbore 244 of the bore 240. The tapered extension 242 may have a threaded hole 246. The neck 122 may also have a shoulder 248, which may protrude from the intramedullary canal of the femur 102 after implantation of the hip prosthesis 110.

The fastening system 114 may include a bolt 250 and a washer 252. The bolt 250 may have a head 260, a threaded distal end 262, and a shank 264 extending from the head 260 to the threaded distal end 262. The washer 252 may have a head engagement surface 270 and a ring engagement surface 272. Prior to use of the fastening system 114, the stem 120 and the neck 122 may be assembled as shown in FIGS. 2A-3, with the tapered extension 242 of the stem 120 residing in the counterbore 244 of the bore 240 of the neck 122. Thus, the stem 120 and the neck 122 may be provisionally attached together, for example, via a press fit between the tapered extension 242 and the counterbore 244.

The bolt 250 may be inserted through the ring 138 of the bone plate 112 and into the bore 240 of the neck 122 such that the threaded distal end 262 of the bolt 250 is inserted into the threaded hole 246 of the tapered extension 242. The head 260 may then be rotated, for example, with a driver (not shown) that mates with a complementary shape formed in the head 260, to cause the threaded distal end 262 of the bolt 250 to engage the threads of the threaded hole 246. The bolt 250 may be tightened such that the head 260 is drawn to compress the ring 138 and the washer 252 between the head 260 and the shoulder 248 of the neck 122. This tightening of the bolt 250 may secure the stem 120 to the neck 122, and may also secure the bone plate 112 to the hip prosthesis 110.

After the bolt 250 has been tightened, the bone plate 112 may be deformed as needed to cause the bone plate 112 to conform more closely to the shape of the greater trochanter 108 and the proximal surface of the femur 102. In some embodiments, the bone plate 112 may not be secured to the femur 102 until after the bone plate 112 has been secured to the hip prosthesis 110. A pair of pliers (not shown) or other instrumentation may be used to bend the bone plate 112 to the desired shape prior to attachment of the bone plate 112 to the femur 102.

In some embodiments, it may be desirable for the bone plate 112 to have a polyaxially-adjustable attachment to the hip prosthesis 110, so that the orientation of the bone plate 112, relative to the hip prosthesis 110, can be adjusted via rotation about at least two orthogonal axes. Further, in some embodiments, adjustability about three orthogonal axes may be provided. The hip implant system 100 may provide such adjustability, as will be shown and described in connection with FIG. 3.

FIG. 3 shows the fastening system 114 and the first and second attachment interfaces 300, 310 of the hip implant system 100 of FIGS. 1A-2B. Specifically, the portion of the hip prosthesis 110 that is secured to the bone plate 112, i.e., the shoulder 248 of the neck 122, may define a first attachment interface 300. Similarly, the portion of the bone plate 112 that is secured to the hip prosthesis 110, i.e., the ring 138, may define a second attachment interface 310. The first attachment interface 300 and the second attachment interface 310 may be shaped to allow the polyaxial adjustability mentioned previously.

Specifically, the first attachment interface 300 may be a dome with a generally semispherical shape with a first radius 320. Similarly, the second attachment interface 310 on the bottom of the ring 138 may be a recess with a semispherical spherical shape that is complementary to that of the dome of the first attachment interface 300. The recess may also be curved at the first radius 320, or at a second radius that is substantially equal to the first radius 320. Thus, before the bolt 250 is tightened, the position and orientation of the ring 138 on the shoulder 248 may be adjusted. Such adjustment may include rotation about any of three axes, for example, a longitudinal axis 350, a lateral axis 360, and a transverse axis 370. Since the ring 138 may move along an arcuate pathway on the first attachment interface 300 of the shoulder 248, such adjustment may further include some translation along the lateral axis 360 and/or the transverse axis 370. Thus, the position and/or orientation of the bone plate 112 relative to the hip prosthesis 110 may be adjusted for optimal positioning of the bone plate 112 on the femur 102.

In some embodiments, the first attachment interface 300 and the second attachment interface 310 may be textured so as to promote secure fixation together when the bolt 250 is tightened. For example, the first attachment interface 300 and the second attachment interface 310 may be knurled or otherwise roughened with any known pattern. In some embodiments, one or both of the first attachment interface 300 and the second attachment interface 310 may deform in response to tightening of the bolt 250 to provide additional secure fixation.

Further, any of the components of the hip implant system 100, or any other implant system described herein, may have a coating or surface texturing that promotes bone in-growth. In some embodiment, nano-textured surfaces may be present. In some configurations, such surfaces may have protrusions and recesses that engage each other in a manner that may be termed "metal Velcro." For example, the first attachment interface 300 and the second attachment interface 310 may each have such nano-texturing, with a matrix of protrusions and recesses on each of the first attachment interface 300 and the second attachment interface 310 such that the protrusions in each engage the recesses in the other. Thus, a very secure fixation may be obtained between the hip prosthesis 110 and the bone plate 112. Such texturing may be used in other mating components of the any implant system described herein.

Figure 4A:
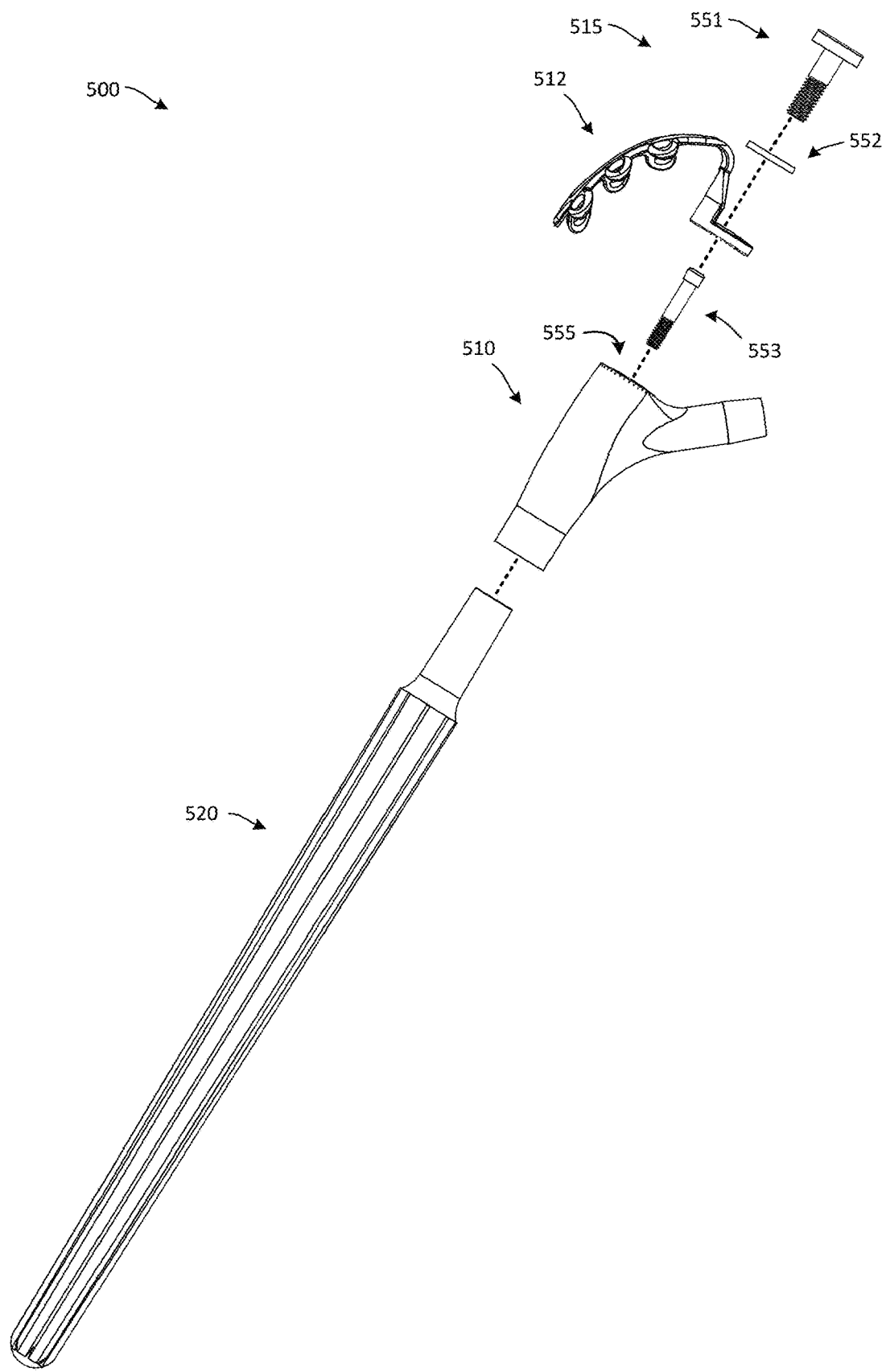
FIG. 4A illustrates an exploded view of a hip implant system 500, according to another embodiment of the present disclosure.
Figure 4B:
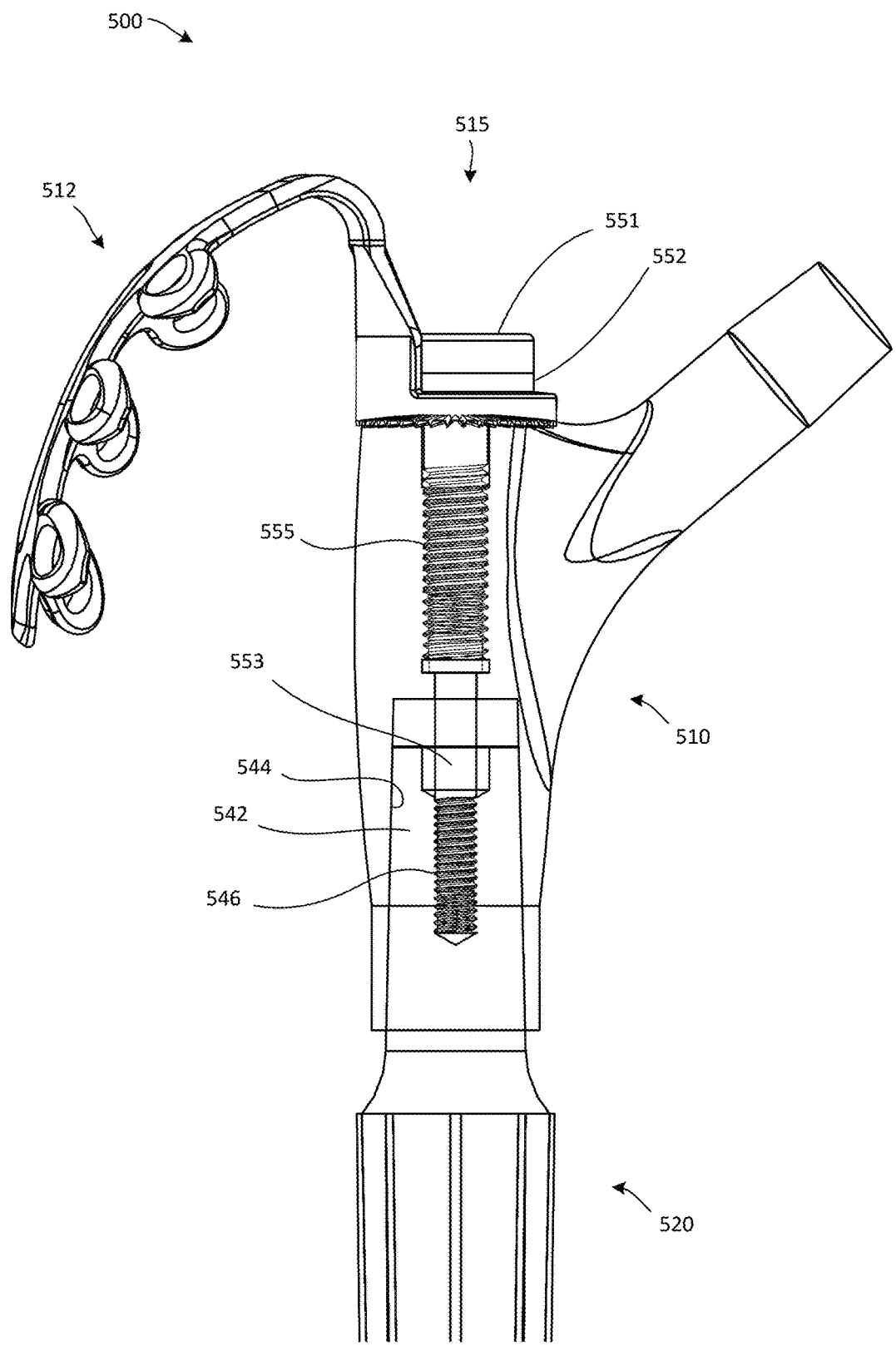
FIG. 4B illustrates a side view of the hip implant system 500 of FIG. 4A in assembled form.

FIGS. 4A and 4B illustrate two different views of a hip implant system 500 incorporating an alternative fastening system 515 configured to separately couple the bone plate 512 and the stem 520 to the hip prosthesis 510. Specifically, FIG. 4A illustrates an exploded view of the hip implant system 500 and FIG. 4B illustrates a side view of the hip implant system 500 assembled together. FIG. 4B also illustrates the hip prosthesis 510 and the stem 520 as "see-through" parts, in order to better illustrate how the first and second fasteners 551, 553 may be utilized to couple the bone plate 512 and the stem 520 to the hip prosthesis 510.

Specifically, the first fastener 551 and washer 552 may be utilized to couple the bone plate 512 to the hip prosthesis 510 via a threaded hole 555 formed in the proximal end of the hip prosthesis 510. The stem 520 may also be separately coupled to the hip prosthesis 510 via the second fastener 553. In the embodiment shown, the second fastener 553 may have a smaller diameter than the first fastener 551 to allow the second fastener 553 to pass through the threaded hole 555 formed in the proximal end of the hip prosthesis 510 and secure the stem 520 to the hip prosthesis 510. The stem 520 may have a tapered extension 542 that may be inserted into a counterbore 544 formed in the distal end of the hip prosthesis 510. The tapered extension 542 may also have a threaded hole 546 formed therein. In this manner, the stem 520 may be coupled to the hip prosthesis 510 via a press fit formed between the tapered extension 542 and the counterbore 544 as the second fastener 553 engages the threaded hole 546 formed in the tapered extension 542. In this manner, both the bone plate 512 and the stem 520 may each be separately and independently couplable to the hip prosthesis 510. It will also be understood that the first and second fasteners 551, 553 may be bolts, screws, or any other suitable fastener known in the art.

In at least some embodiments, the proximal end of the hip prosthesis 510 may additionally include a keyed hole and/or at least one surface configured to allow for rotational adjustment of the bone plate 512 with respect to the hip prosthesis 510, as will be described below in more detail with respect to FIGS. 7A-9B.

Figure 5:
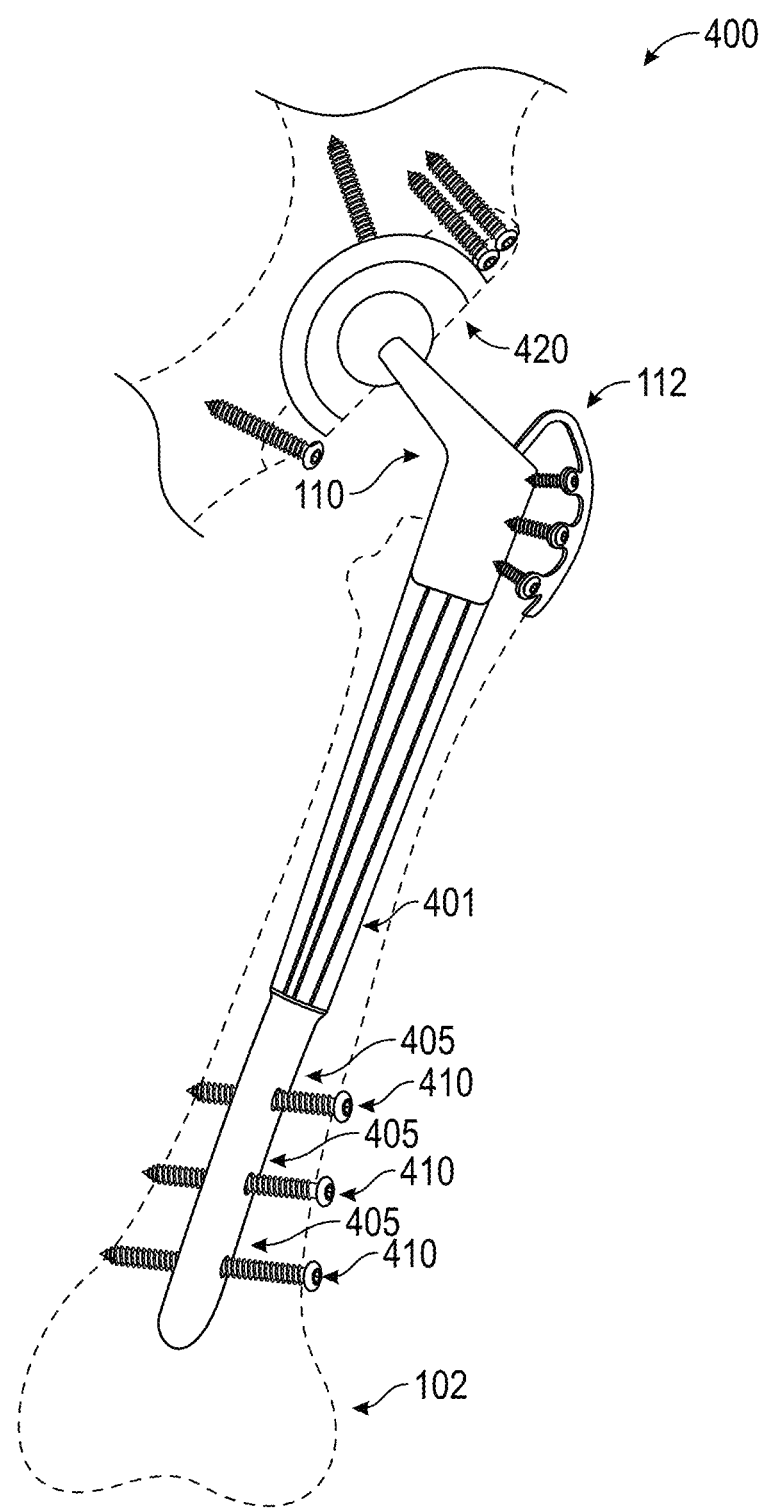
FIG. 5 illustrates a front elevation, section view of a hip implant system 400, according to another embodiment of the present disclosure.

FIG. 5 illustrates a front elevation, section view of a hip implant system 400 coupled to an acetabular cup 420 via the hip prosthesis 110 which is also coupled to the bone plate 112. The hip implant system 400 may be similar in construction to other hip implant systems described herein. However, the stem 401 of the hip implant system 400 may additionally include one or more transverse passages 405 formed in the distal end of the stem 401 which may be configured to receive one or more fasteners 410 therethrough in order to provide additional securement of the stem 401 to the femur 102.

Figure 6:
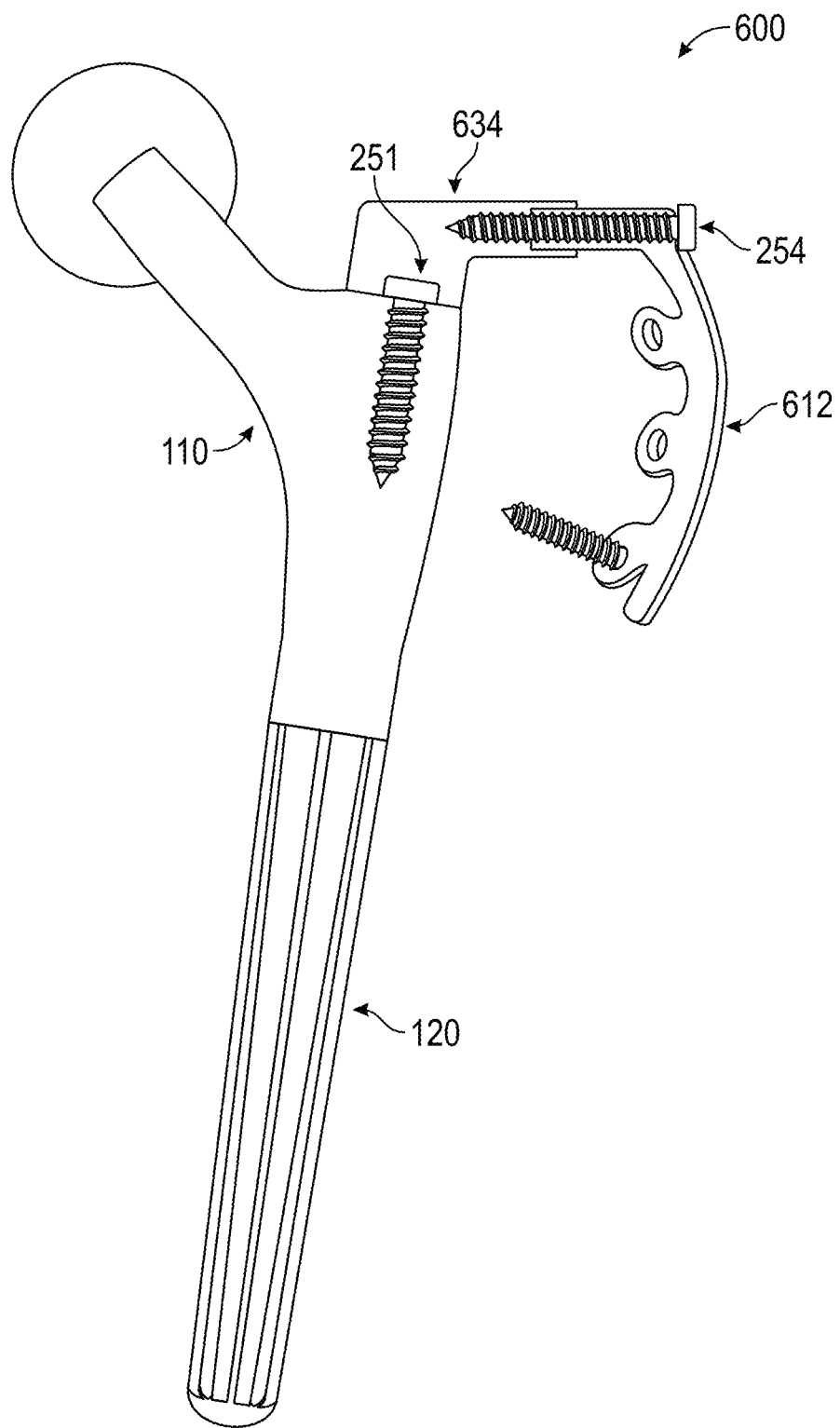
FIG. 6 illustrates a front elevation, section view of a hip implant system 600, according to another embodiment of the present disclosure.

FIG. 6 illustrates a front elevation, section view of a hip implant system 600, according to another embodiment of the present disclosure. The hip implant system 600 may be similar in construction to other hip implant systems described herein. However, the hip implant system 600 may additionally include an adjustable arm mechanism 634 that may be configured to adjustably couple the bone plate 612 to the hip prosthesis 110 at a plurality of different distances with respect to the hip prosthesis 110. The adjustable arm mechanism 634 may be coupled to the hip prosthesis 110 via a first fastener 251. The bone plate 612 may be coupled to the adjustable arm mechanism 634 via a second fastener 254. The second fastener 254 may be configured to move the bone plate 612 toward the hip prosthesis 110 in order to compress the bone plate 612 against a greater trochanter of a femur (not shown in FIG. 6), as the second fastener 254 is threadably engaged with the adjustable arm mechanism 634. Conversely, the second fastener 254 may be configured to move the bone plate 612 away from the hip prosthesis 110 in order to decompress the bone plate 612 away from the greater trochanter of the femur, as the second fastener 254 is threadably disengaged with the adjustable arm mechanism 634. In this manner, the adjustable arm mechanism 634 may provide for additional conformity of the bone plate 612 with respect to the greater trochanter of the femur. Moreover, in at least some embodiments, the adjustable arm mechanism 634 may be further configured to rotate about the hip prosthesis 110 via a keyed or toothed mechanism/connection (not shown in FIG. 6) formed between the adjustable arm mechanism 634 and the hip prosthesis 110, as will be discussed below in more detail with respect to FIGS. 7A and 7B.

Figure 7A:
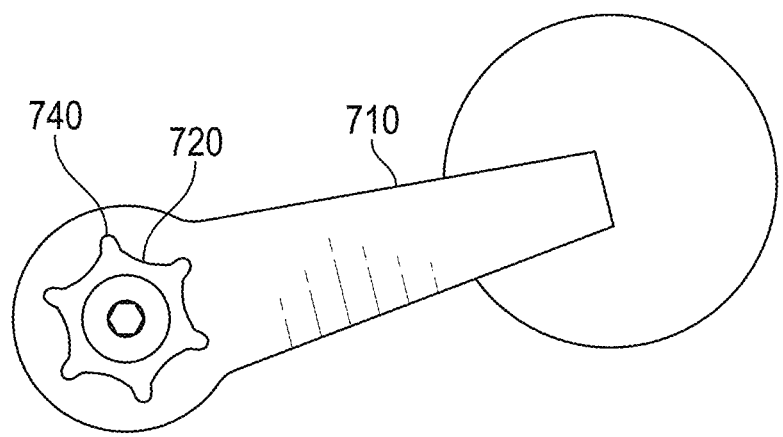
FIG. 7A illustrates a top view of a hip prosthesis 710 with a keyed hole 720 formed therein, according to another embodiment of the present disclosure.
Figure 7B:
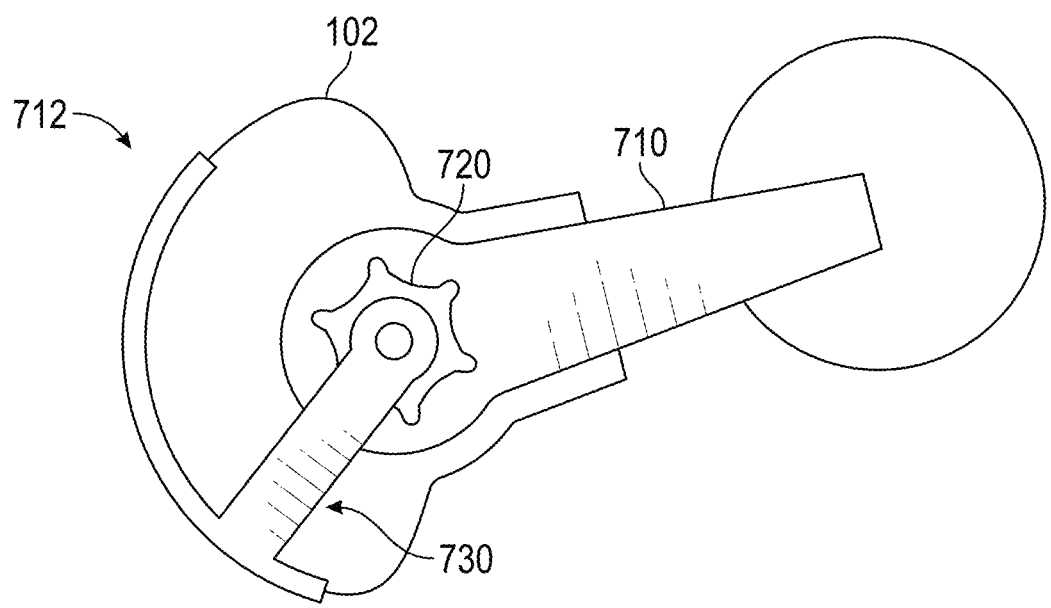
FIG. 7B illustrates a top view of the hip prosthesis 710 of FIG. 7A coupled to a bone plate 712 via an offset arm 730.

FIGS. 7A and 7B illustrate two top views of a hip prosthesis 710, according to another embodiment of the present disclosure. Specifically, FIG. 7A shows a top view of the hip prosthesis 710 illustrating a keyed hole 720 formed in the proximal end of the hip prosthesis 710 and FIG. 7B shows a top view of the hip prosthesis 710 coupled to a bone plate 712 via an offset arm 730. The keyed hole 720 may include one or more recesses 740 which may be shaped and/or configured to receive one or more complementarily shaped teeth (not shown) formed on the offset arm 730 at the point where the offset arm 730 connects to the hip prosthesis 710 via insertion into the keyed hole 720. In this manner, the bone plate 712 may be selectively rotated relative to the hip prosthesis 710 in order to adjust an angular position of the bone plate 712 with respect to the hip prosthesis 710 in order to achieve a better conformity of the bone plate 712 with a surface of the femur 102. Moreover, the offset arm 730 may also help facilitate better positioning of the bone plate 712 with respect to the femur 102 and/or the hip prosthesis 710, as the bone plate 712 is selectively rotated and positioned relative to the hip prosthesis 710. Once the bone plate 712 has been selectively rotated and positioned relative to the hip prosthesis 710, the bone plate 712 may be secured to the hip prosthesis 710 via a suitable fastener (not shown) which may be inserted through the offset arm 730 and into the keyed hole 720.

Figure 8A:
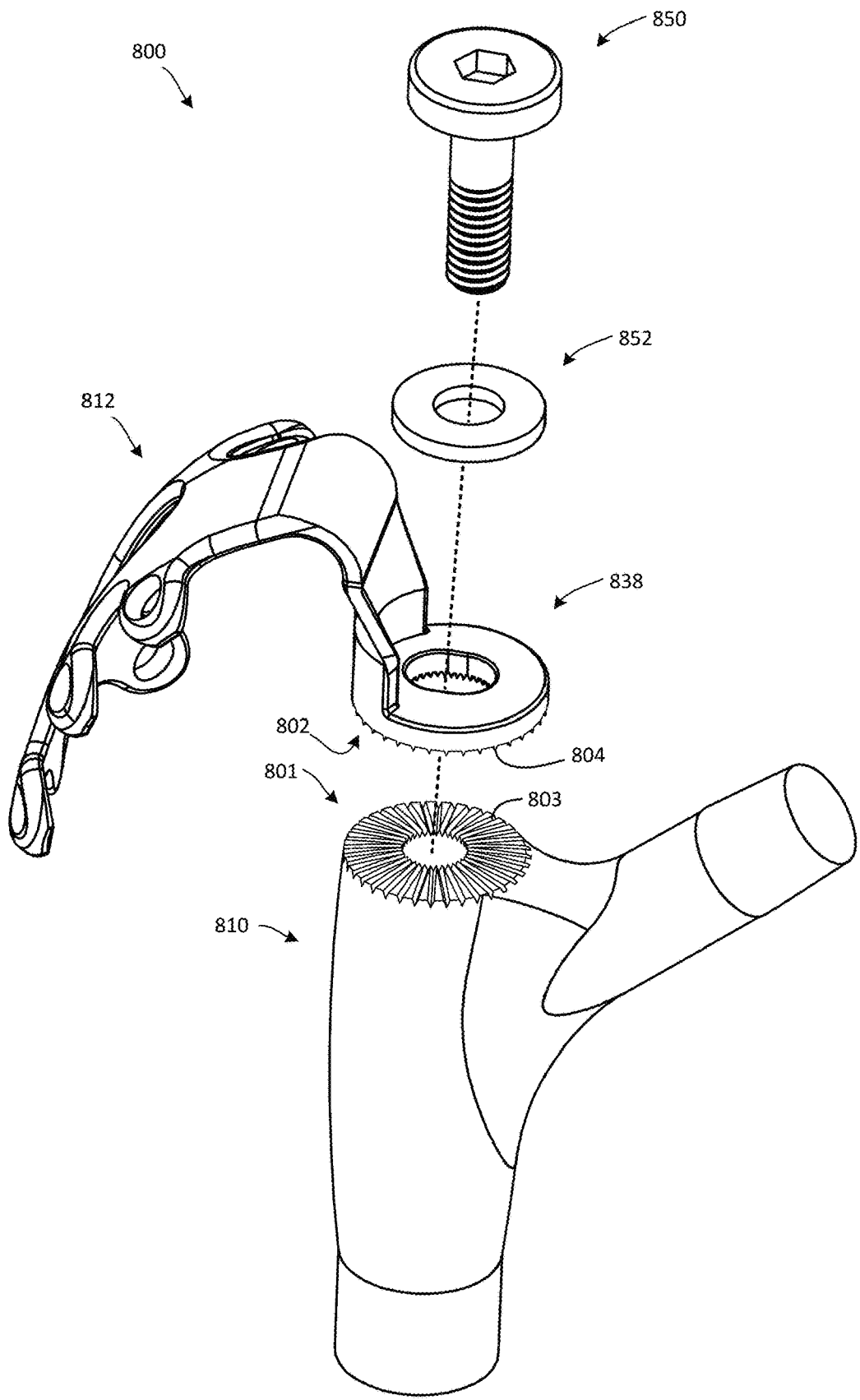
FIG. 8A illustrates an exploded top view of a hip implant system 800, according to another embodiment of the present disclosure.
Figure 8B:
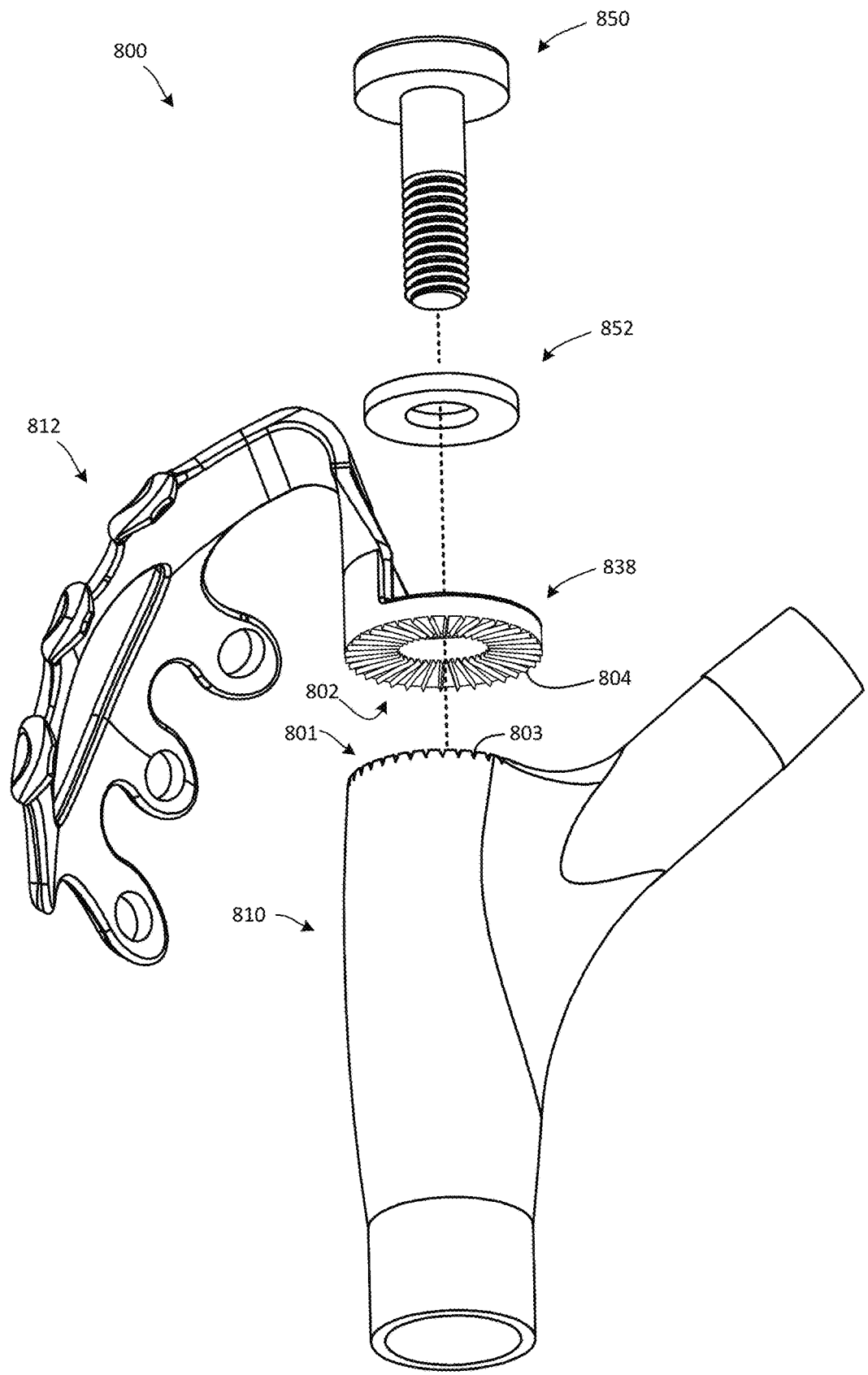
FIG. 8B illustrates an exploded bottom view of the hip implant system 800 of FIG. 8A.

FIGS. 8A and 8B illustrate exploded views of another example hip implant system 800 including a hip prosthesis 810 and a bone plate 812 that may rotate relative to the hip prosthesis 810. The hip implant system 800 may also include a hip stem (not shown) which may be coupled to the distal end of the hip prosthesis 810.

The bone plate 812 may be coupled to the proximal end of the hip prosthesis 810 via the fastener 850 and washer 852. The fastener 850 and washer 852 may be configured to apply a compression force to the ring 838 of the bone plate 812 in order to couple the bone plate 812 to the hip prosthesis 810. The bone plate 812 may be rotated to any number of different discrete angular positions relative to the hip prosthesis 810 prior to securing the bone plate 812 to the hip prosthesis 810. The distal surface 802 of the ring 838 may include one or more teeth 804 formed thereon and the proximal surface 801 of the hip prosthesis 810 may include one or more recesses 803 formed therein. The one or more teeth 804 formed on the distal surface 802 of the ring 838 may be configured to fit within the one or more recesses 803 formed in the proximal surface 801 of the hip prosthesis 810, in order to prevent the bone plate 812 from further rotation with respect to the hip prosthesis 810 after the bone plate 812 has been secured to the hip prosthesis 810. In this manner, the attachment interfaces between the bone plate 812 and the hip prosthesis 810 may be configured to allow for rotational adjustment of the bone plate 812 with respect to the hip prosthesis 810 to any number of different selectable discrete angular or rotational positions.

Figure 9A:
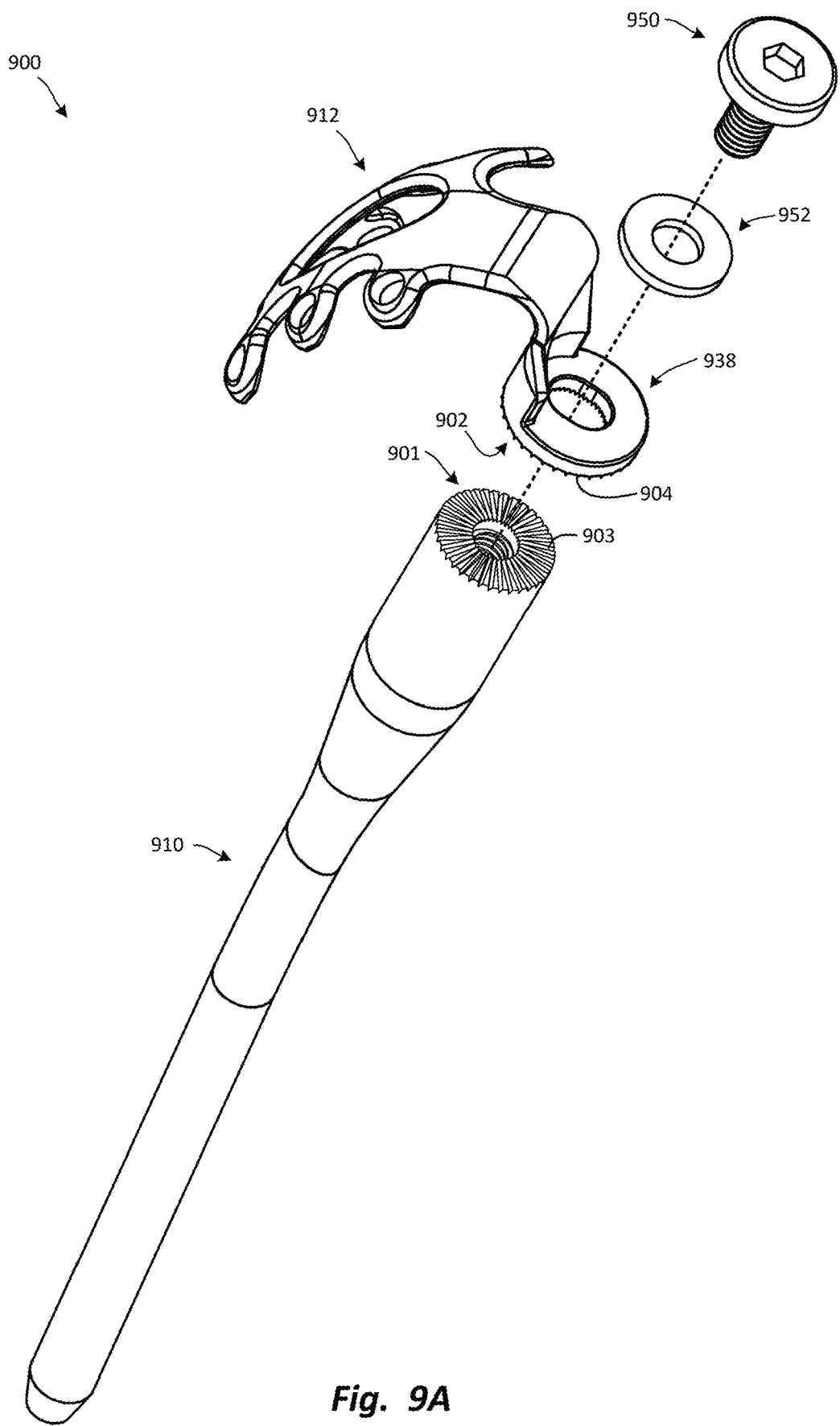
FIG. 9A illustrates an exploded top view of a hip implant system 900, according to another embodiment of the present disclosure.
Figure 9B:
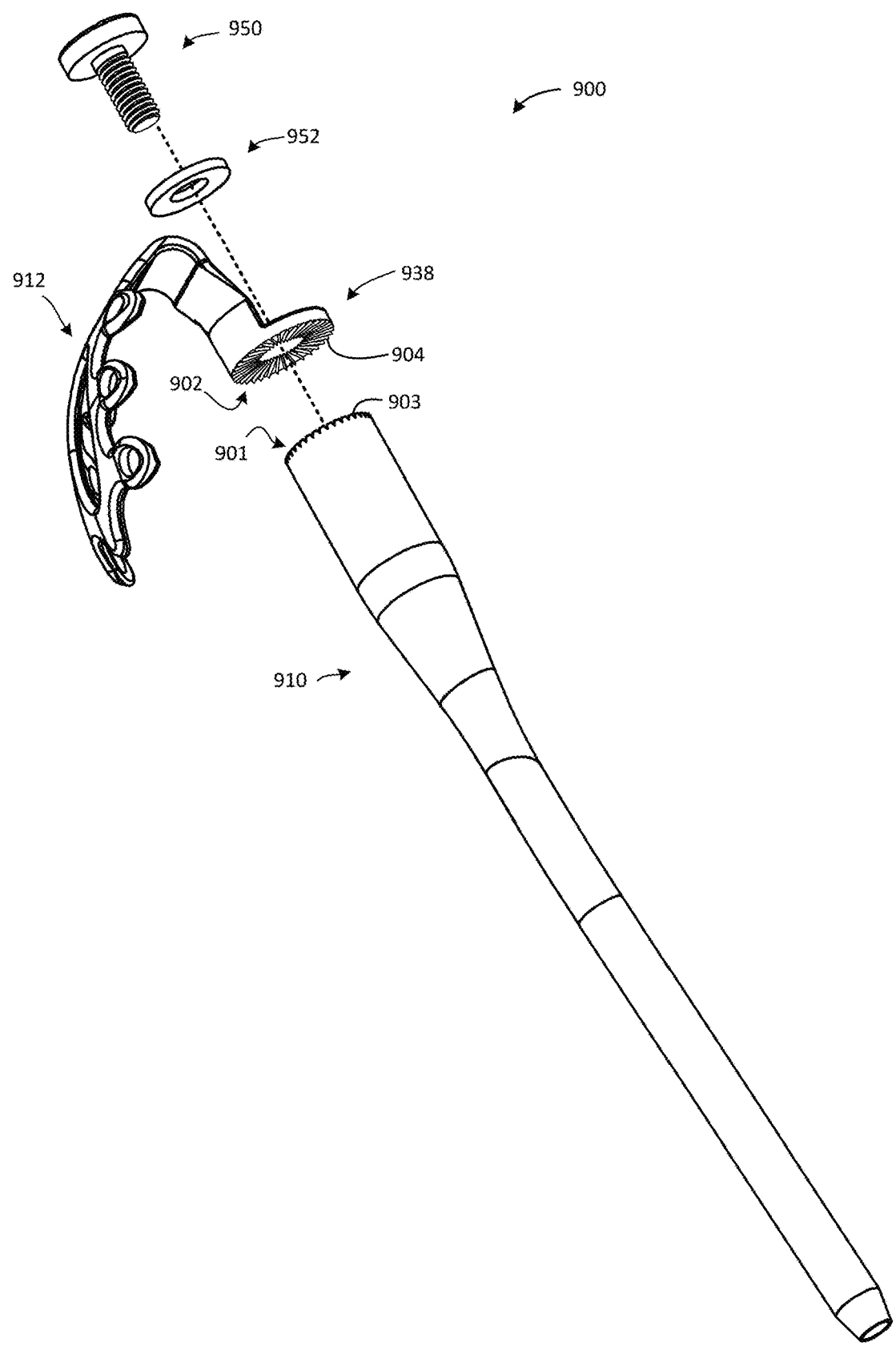
FIG. 9B illustrates an exploded bottom view of the hip implant system 900 of FIG. 9A.

FIGS. 9A and 9B illustrate exploded views of another example hip implant system 900 including an intramedullary nail 910 and a bone plate 912 that may rotate relative to the intramedullary nail 910. The bone plate 912 may be coupled to the proximal end of the intramedullary nail 910 via the fastener 950 and washer 952. The fastener 950 and washer 952 may be configured to apply a compression force to the ring 938 of the bone plate 912 in order to couple the bone plate 912 to the intramedullary nail 910. The bone plate 912 may be rotated to any number of different discrete angular positions relative to the intramedullary nail 910 prior to securing the bone plate 912 to the intramedullary nail 910. The distal surface 902 of the ring 938 may include one or more teeth 904 formed thereon and the proximal surface 901 of the intramedullary nail 910 may include one or more recesses 903 formed therein. The one or more teeth 904 formed on the distal surface 902 of the ring 938 may be configured to fit within the one or more recesses 903 formed in the proximal surface 901 of the intramedullary nail 910, in order to prevent the bone plate 912 from further rotation with respect to the intramedullary nail 910 after the bone plate 912 has been secured to the intramedullary nail 910. In this manner, the attachment interfaces between the bone plate 912 and the intramedullary nail 910 may be configured to allow for rotational adjustment of the bone plate 912 with respect to the intramedullary nail 910 to any number of different selectable discrete angular or rotational positions.

It will be understood that any other suitable features may also be implemented to achieve discrete angular or rotational adjustment of the bone plate with respect to the joint replacement prosthesis including, but not limited to: Torx shaped features, hex shaped features, or any multi-side polygon shaped features, etc.

In other embodiments (not shown), the attachment interfaces between the bone plate and the joint replacement prosthesis may be configured to allow for an infinite number of rotational adjustment positions between the bone plate and the joint replacement prosthesis via a friction locking mechanism. For example, each of the attachment interfaces may be textured so as to promote secure fixation when the attachment interfaces are coupled together via a compression force. For example, the attachment interfaces may be knurled, bead-blasted, sprayed with metal plasma, shot-peened, acid-etched, or otherwise roughened with any known pattern that may form interlocking positive and negative features on opposing surfaces to resist rotation and/or shear and form surfaces that are a friction-locked together. In some embodiments, one or both of the attachment interfaces may deform in response to a compression force to provide additional secure fixation. In some configurations, the attachment interfaces may have protrusions and recesses that engage each other in a manner that may be termed "metal Velcro." For example, the attachment interfaces may each have nano-texturing, with a matrix of protrusions and recesses on each of the attachment interfaces such that the protrusions in each engage the recesses in the other. Examples of such surface texturing may be found in at least PCT Application No. PCT/US19/16697 entitled "MEDICAL IMPLANT SURFACE TREATMENT AND METHOD" filed on Feb. 5, 2019 and claiming priority to U.S. Provisional Patent Application Ser. No. 62/626,479, which was filed on Feb. 5, 2018. Both of these references are incorporated herein by reference in their entirety.

Figure 10:
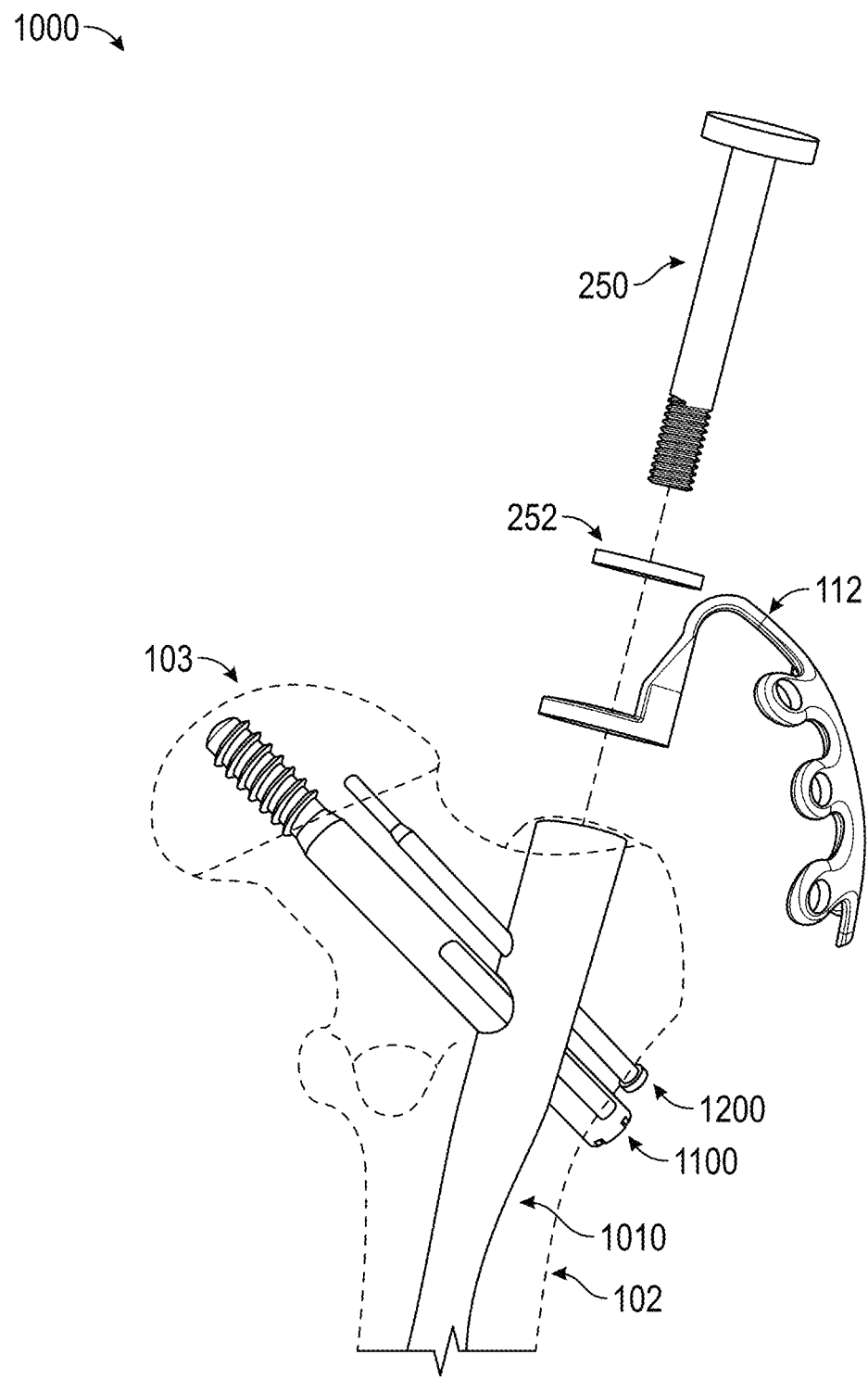
FIG. 10 illustrates an exploded view of a hip implant system 1000, according to another embodiment of the present disclosure.
Figure 11:
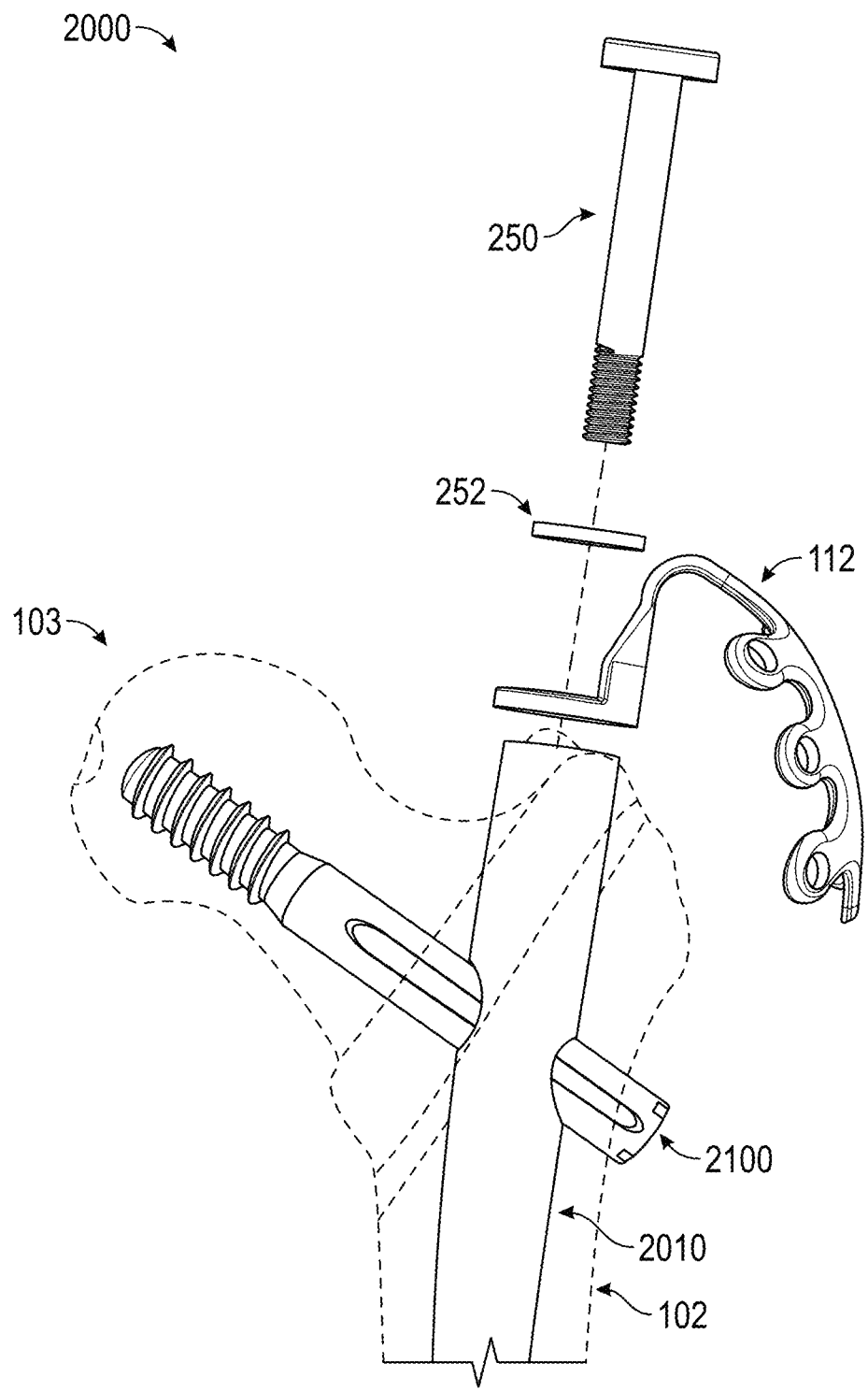
FIG. 11 illustrates an exploded view of a hip implant system 2000, according to another embodiment of the present disclosure.
Figure 12:
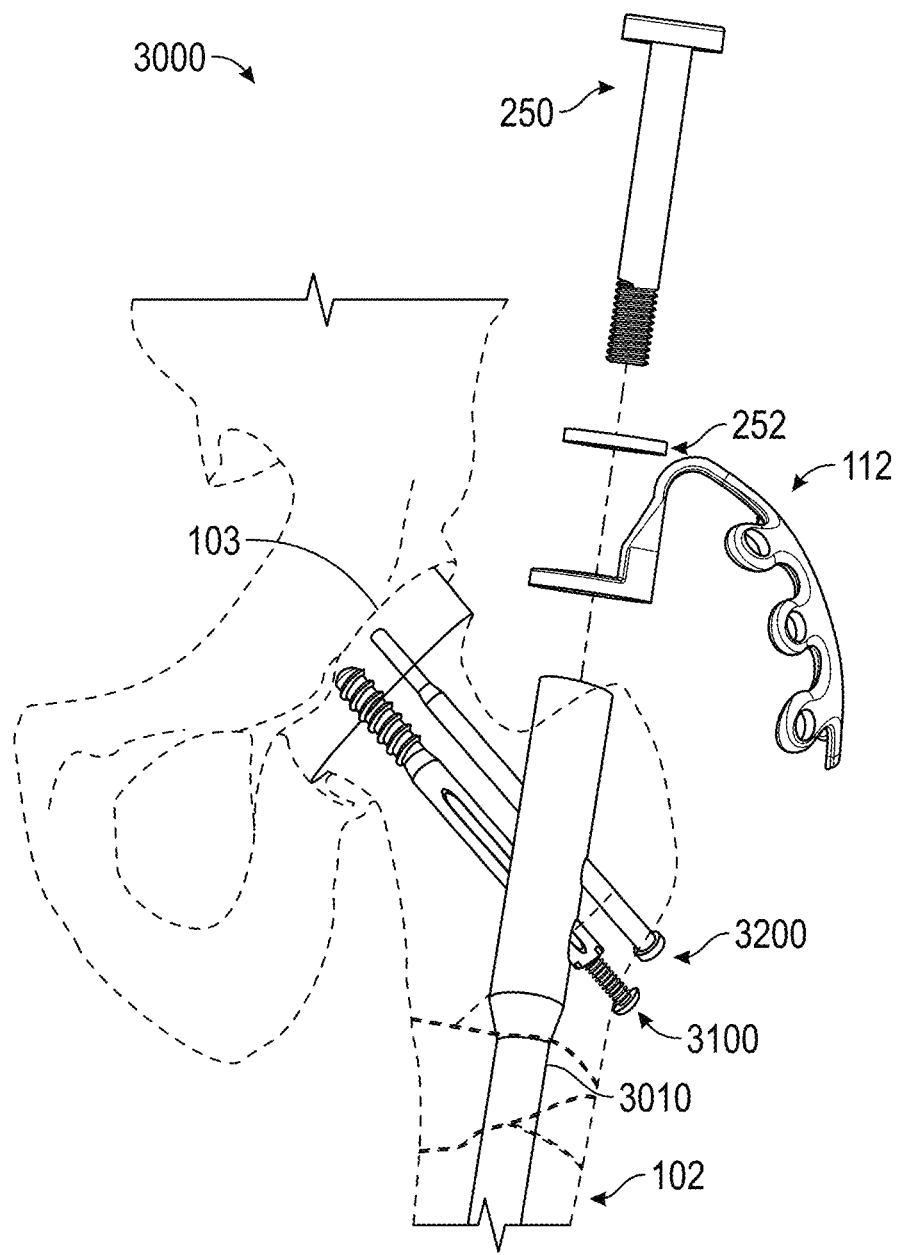
FIG. 12 illustrates an exploded view of a hip implant system 3000, according to another embodiment of the present disclosure.
Figure 13:
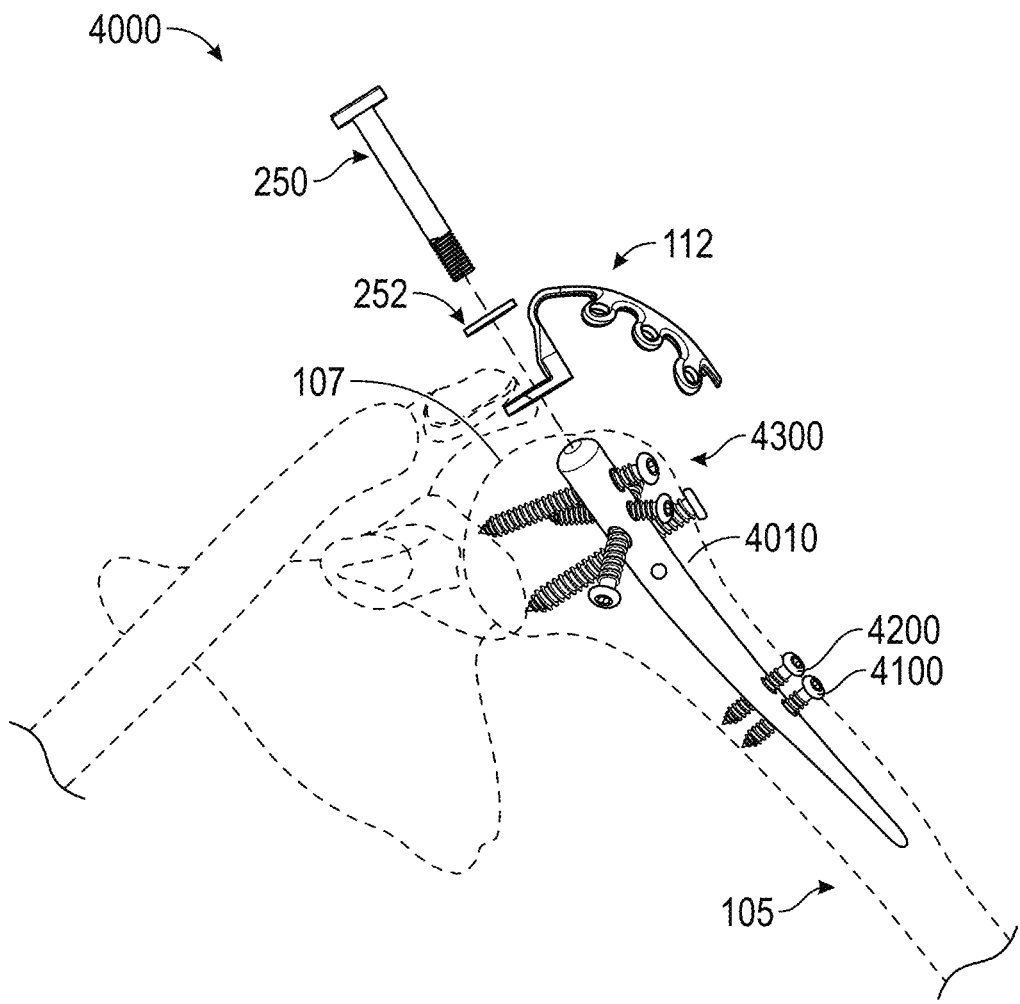
FIG. 13 illustrates an exploded view of a humeral implant system 4000, according to another embodiment of the present disclosure.

FIGS. 10-13 illustrate various examples of implant systems that may be configured to utilize a bone plate coupled to an implant. Specifically, FIG. 10 illustrates an exploded view of an example hip implant system 1000 configured to utilize a bone plate that may be coupled to the implant shown in FIG. 10; FIG. 11 illustrates an exploded view of another example hip implant system 2000 configured to utilize a bone plate that may be coupled to the implant shown in FIG. 11; FIG. 12 illustrates an exploded view of another hip implant system 3000 configured to utilize a bone plate that may be coupled to the implant shown in FIG. 12; and FIG. 13 illustrates an exploded view of a humeral implant system 4000 configured to utilize a bone plate that may be coupled to the implant shown in FIG. 13.

However, it will also be understood that the implants, systems, and methods presented herein are merely exemplary. Those of skill in the art will recognize that the principles set forth herein could be applied to a wide variety of surgical procedures and implants. In particular, the implants, systems, and methods set forth herein are not limited to femoral hip implants or femoral greater trochanter plates, but may be used for a wide variety of joint arthroplasties, joint hemi-arthroplasties, and/or bone fractures. For example, such joint replacement prostheses may include, but are not limited to, femoral joint replacement prostheses, tibial joint replacement prostheses, fibular joint replacement prostheses, humeral joint replacement prostheses, clavicle joint replacement prostheses, radial joint replacement prostheses, ulnar joint replacement prostheses, digital joint replacement prostheses, intramedullary nails, etc. Moreover, each of these replacement prostheses may be combined with any bone plate system described herein.

FIG. 10 illustrates an exploded view of an example hip implant system 1000 configured to utilize the bone plate 112. The hip implant system 1000 may include an intramedullary nail 1010 inserted within an intramedullary canal of the femur 102, a first hip prosthesis member 1100 providing support to the femoral head 103 via the intramedullary nail 1010, and a second hip prosthesis member 1200 providing additional support to the femoral head 103 via the intramedullary nail 1010. The hip implant system 1000 may also be coupled to the bone plate 112 via the bolt 250 and washer 252, in a similar fashion to other hip implant systems described herein. In at least one embodiment, the hip implant system 1000 may also be polyaxially-adjustable relative to the bone plate 112, such that the bone plate 112 can be adjusted via rotation about at least two orthogonal axes. In other embodiments, the hip implant system 1000 may be polyaxially-adjustable relative to the bone plate 112 about three orthogonal axes.

FIG. 11 illustrates an exploded view of another example hip implant system 2000 configured to utilize the bone plate 112. The hip implant system 2000 may include an intramedullary nail 2010 inserted within an intramedullary canal of the femur 102, and a hip prosthesis member 2100 providing support to the femoral head 103 via the intramedullary nail 2010. The hip implant system 2000 may also be coupled to the bone plate 112 via the bolt 250 and washer 252, in a similar fashion to other hip implant systems described herein. In at least one embodiment, the hip implant system 2000 may be polyaxially-adjustable relative to the bone plate 112, such that the bone plate 112 can be adjusted via rotation about at least two orthogonal axes. In other embodiments, the hip implant system 2000 may be polyaxially-adjustable relative to the bone plate 112 about three orthogonal axes.

FIG. 12 illustrates an exploded view of another example hip implant system 3000 configured to utilize the bone plate 112. The hip implant system 3000 may include an intramedullary nail 3010 inserted within an intramedullary canal of the femur 102, a first hip prosthesis member 3100 providing support to the femoral head 103 via the intramedullary nail 3010, and a second hip prosthesis member 3200 providing additional support to the femoral head 103 via the intramedullary nail 3010. The hip implant system 3000 may also be coupled to the bone plate 112 via the bolt 250 and washer 252, in a similar fashion to other hip implant systems described herein. In at least one embodiment, the hip implant system 3000 may be polyaxially-adjustable relative to the bone plate 112, such that the bone plate 112 can be adjusted via rotation about at least two orthogonal axes. In other embodiments, the hip implant system 3000 may be polyaxially-adjustable relative to the bone plate 112 about three orthogonal axes.

FIG. 13 illustrates an exploded view of an example humeral implant system 4000 configured to utilize the bone plate 112. The humeral implant system 4000 may include an intramedullary nail 4010 inserted within an intramedullary canal of the humerus 105, a first fastener 4100 and a second fastener 4200 to couple the intramedullary nail 4010 to the humerus 105, and one or more fasteners 4300 to provide support for the humeral head 107 via the intramedullary nail 4010. The humeral implant system 4000 may also be coupled to a bone plate 112 via the bolt 250 and washer 252 in similar fashion to other implant systems described herein. In at least one embodiment, the humeral implant system 4000 may be polyaxially-adjustable relative to the bone plate 112, such that the bone plate 112 can be adjusted via rotation about at least two orthogonal axes. In other embodiments, the humeral implant system 4000 may be polyaxially-adjustable relative to the bone plate 112 about three orthogonal axes.

Figure 14:
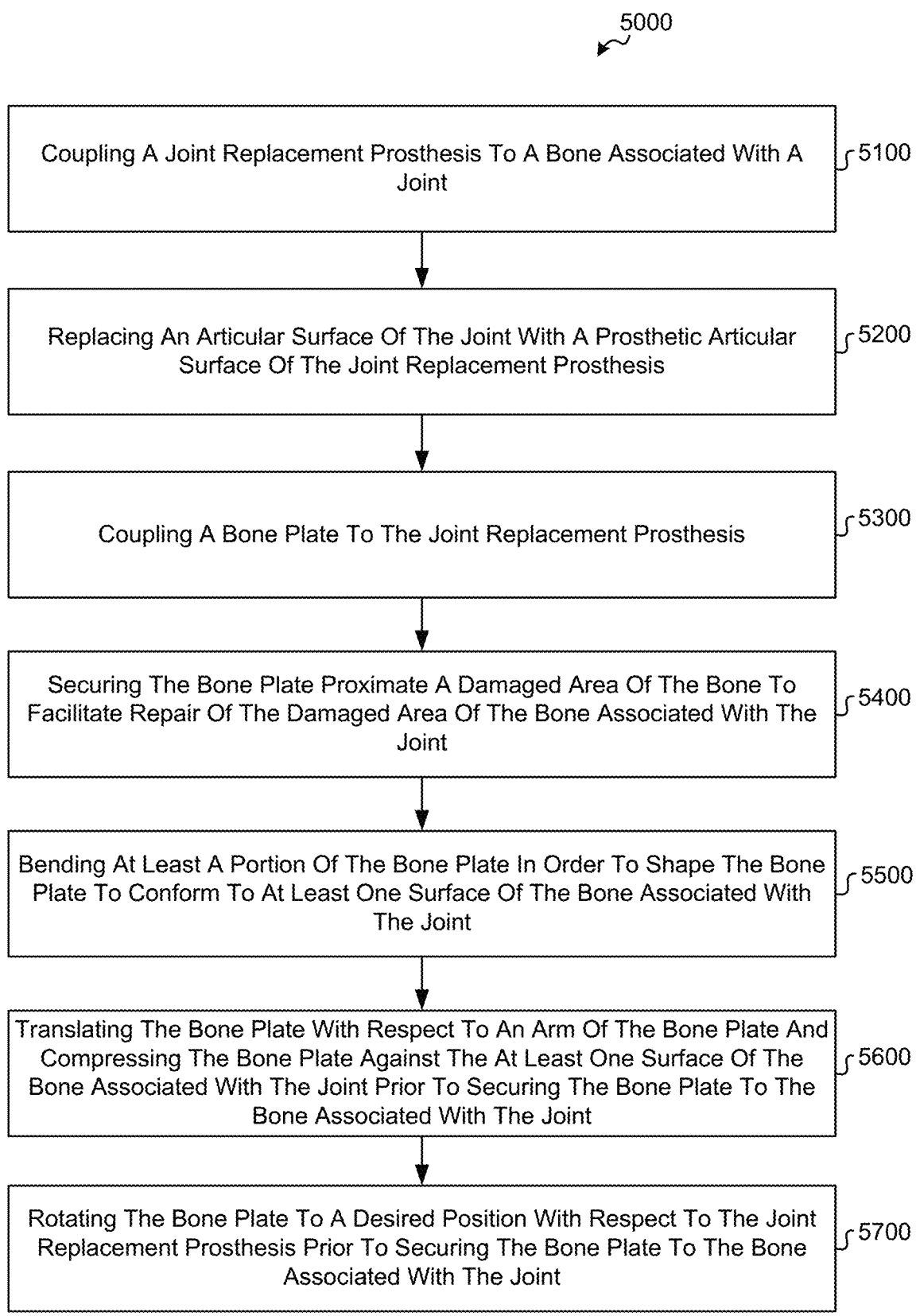
FIG. 14 illustrates a flowchart of a method 5000 for replacing a natural or artificial articular surface of a joint and repairing a bone associated with the joint, according to an embodiment of the disclosure.

FIG. 14 illustrates a flowchart of a method 5000 for replacing a natural or artificial articular surface of a joint and repairing a bone associated with the joint, according to an embodiment of the disclosure.

The method 5000 may begin with a step 5100 in which a joint replacement prosthesis may be coupled to a bone that is associated with a joint. The joint replacement prosthesis may include any type of joint replacement prosthesis including, but not limited to, femoral joint replacement prostheses, tibial joint replacement prostheses, fibular joint replacement prostheses, humeral joint replacement prostheses, clavicle joint replacement prostheses, radial joint replacement prostheses, ulnar joint replacement prostheses, digital joint replacement prostheses, intramedullary nails, etc.

Once the joint replacement prosthesis has been coupled to the bone associated with a joint, the method 5000 may proceed to a step 5200 in which an articular surface of the joint may be replaced with a prosthetic articular surface of the joint replacement prosthesis. However, it will also be understood that in other embodiments, an articular surface of the joint may not be replaced with a prosthetic articular surface of the joint replacement prosthesis. For example, a hip joint replacement prosthesis that comprises an intramedullary nail may not include any additional structures that may replace an articular surface of the hip joint with a prosthetic articular surface.

Once the articular surface of the joint may have been replaced with a prosthetic articular surface of the joint replacement prosthesis, the method 5000 may proceed to a step 5300 in which a bone plate may be coupled to the joint replacement prosthesis. The bone plate may be coupled to the joint replacement prosthesis via any method described herein, or via any other suitable method known in the art.

Once the bone plate has been coupled to the joint replacement prosthesis, the method 5000 may proceed to a step 5400 in which the bone plate may be secured proximate a damaged area of the bone, in order to facilitate repair of the damaged area of the bone associated with the joint. In at least one embodiment, the damaged area of the bone may include a fracture that is formed in the bone associated with the joint.

Alternatively, or in addition thereto, the method 5000 may proceed to a step 5500 in which at least a portion of the bone plate may be bent in order to shape the bone plate to conform to at least one surface of the bone associated with the joint. The bone plate may be bent prior to being secured proximate the damaged area of the bone.

Alternatively, or in addition thereto, the method 5000 may proceed to a step 5600 in which the bone plate may be translated with respect to an arm of the bone plate. The bone plate may also be compressed against the at least one surface of the bone associated with the joint, prior to securing the bone plate to the bone associated with the joint.

Alternatively, or in addition thereto, the method 5000 may proceed to a step 5700 in which the bone plate may be rotated to a desired position with respect to the joint replacement prosthesis, prior to securing the bone plate to the bone associated with the joint. The bone plate may be rotated with respect to the joint replacement prosthesis according to discrete or infinite rotational positions, as described herein, and the method 5000 may end.

Any methods disclosed herein comprise one or more steps or actions for performing the described method. One or more of the method steps and/or actions may be omitted from any of the methods disclosed herein. Moreover, any of the method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of the appended claims is not limited to the precise configuration and components disclosed herein. Various modifications, changes, and variations which will be apparent to those skilled in the art may be made in the arrangement, operation, and details of the methods and systems disclosed herein.

What is claimed is:

1. A system for repairing an end portion of a bone, the system comprising:
   an intramedullary nail comprising:
      a first attachment interface formed on a superior surface of the intramedullary nail;
   a bone plate comprising:
      a bone engagement surface that is securable to an exterior surface of the end portion; and
      a second attachment interface that is attachable to the first attachment interface of the intramedullary nail in order to couple the bone plate to the intramedullary nail;
   a first fastener configured to secure the bone engagement surface to the exterior surface of the bone; and
   a second fastener comprising a longitudinal axis and configured to secure the second attachment interface to the first attachment interface at any of a plurality of relative orientations;
   wherein:
      the bone engagement surface comprises a central aperture configured to reduce a weight and facilitate flexure of the bone plate;
      the bone plate is sufficiently thin to allow the bone engagement surface to be flexed into conformity with the exterior surface; and
      with the second attachment interface secured to the first attachment interface, the longitudinal axis of the second fastener is generally parallel to an axis of the bone.

2. The system of claim 1, wherein the bone plate further comprises:
   at least one arm extending proximate the second attachment interface;
   at least one central expanse coupled to the at least one arm; and
   at least one bone engagement feature coupled to the at least one central expanse,
   wherein one or more of the at least one arm, the at least one central expanse, and the at least one bone engagement feature is bendable, such that one or more of the at least one arm, the at least one central expanse, and the at least one bone engagement feature can be shaped to conform to the exterior surface.

3. The system of claim 2, wherein the bone engagement surface is further securable to the exterior surface on either side of a fracture formed in the end portion of the bone and the at least one central expanse is securable to the exterior surface on:
   a first side of the fracture that is formed in the end portion of the bone, via a first bone engagement feature; and
   a second side of the fracture that is formed in the end portion of the bone, via a second bone engagement feature.

4. The system of claim 1, wherein the bone plate further comprises an arm comprising the bone engagement surface, wherein the arm is shaped such that, with the second attachment interface attached to the first attachment interface, the arm extends towards a distal end of the intramedullary nail.

5. The system of claim 1, wherein the first attachment interface and the second attachment interface are configured to allow for discrete rotational adjustments of the bone plate with respect to the intramedullary nail from among a plurality of different discrete rotational positions.

6. The system of claim 1, wherein the first attachment interface and the second attachment interface are configured to allow for an infinite number of rotational adjustment positions between the bone plate and the intramedullary nail.

7. The system of claim 1, wherein the first attachment interface comprises a proximal surface perpendicular to the axis of the bone.

8. An apparatus for repairing an end portion of a bone, the apparatus comprising:
   an intramedullary nail comprising:

a first attachment interface formed on a proximal surface of the intramedullary nail; and
a distal end opposite the proximal surface;
a bone plate comprising:
an arm comprising:
a bone engagement surface that is securable to an exterior surface of the end portion;
a first plurality of bone engagement features having a first plurality of holes, wherein the first plurality of bone engagement features is positioned such that, with the bone engagement surface secured to the exterior surface, the first plurality of bone engagement features extends anteriorly from the arm on an anterior side of the exterior surface; and
a second plurality of bone engagement features having a second plurality of holes, wherein the second plurality of bone engagement features is positioned such that, with the bone engagement surface secured to the exterior surface, the second plurality of bone engagement features extends posteriorly from the arm on a posterior side of the exterior surface; and
a second attachment interface that is attachable to the first attachment interface of the intramedullary nail in order to couple the bone plate to the intramedullary nail; and
a plurality of bone screws insertable through the first plurality of holes and the second plurality of holes, and through the exterior surface to secure the arm directly to the bone;
wherein the arm is shaped such that, with the second attachment interface attached to the first attachment interface, the arm extends towards the distal end of the intramedullary nail.

9. The apparatus of claim 8, further comprising:
a fastening system configured to engage the second attachment interface with the first attachment interface and couple the bone plate to the intramedullary nail;
wherein the second attachment interface of the bone plate is attachable to the first attachment interface of the intramedullary nail at any of a plurality of relative orientations.

10. The apparatus of claim 8, wherein the bone plate further comprises at least one central expanse coupled to the arm;
wherein one or more of the arm and the at least one central expanse are bendable, such that one or more of the arm and the at least one central expanse can be shaped to conform to the exterior surface.

11. The apparatus of claim 10, wherein the bone engagement surface is further securable to the exterior surface on either side of a fracture formed in the end portion of the bone and the at least one central expanse further comprises an aperture formed in the at least one central expanse in order to facilitate flexure of the at least one central expanse so that the at least one central expanse can be shaped to conform to the exterior surface;
wherein the at least one central expanse is securable to the bone on:
a first side of the fracture that is formed in the end portion, via the first plurality of holes; and
a second side of the fracture that is formed in the end portion, via the second plurality of holes.

12. The apparatus of claim 10, wherein the arm is configured to allow the at least one central expanse to translate with respect to the arm to in order to compress the at least one central expanse against the exterior surface of the end portion.

13. The apparatus of claim 8, wherein the first attachment interface and the second attachment interface are configured to allow for discrete rotational adjustments of the bone plate with respect to the intramedullary nail from among a plurality of different discrete rotational positions.

14. The apparatus of claim 8, wherein the first attachment interface and the second attachment interface are configured to allow for an infinite number of rotational adjustment positions between the bone plate and the intramedullary nail.

15. A system for repairing an end portion of a bone, the system comprising:
an intramedullary nail comprising:
a first attachment interface formed on a superior surface of the intramedullary nail; and
a bone plate comprising:
an arm comprising a bone engagement surface that is securable to an exterior surface of the end portion;
an anterior bone engagement feature protruding anteriorly of the arm;
a posterior bone engagement feature protruding posteriorly of the arm; and
a second attachment interface that is attachable to the first attachment interface of the intramedullary nail in order to couple the bone plate to the intramedullary nail;
wherein
the anterior bone engagement feature comprises a first eyelet through which a first fastener is insertable to secure the bone plate to the exterior surface;
the posterior bone engagement feature comprises a second eyelet through which a second fastener is insertable to secure the bone plate to the exterior surface; and
the bone plate is sufficiently thin to allow the bone engagement surface to be flexed into conformity with the exterior surface.

16. The system of claim 15, the system further comprising a fastener comprising a longitudinal axis and configured to secure the second attachment interface to the first attachment interface at any of a plurality of relative orientations, wherein, with the second attachment interface secured to the first attachment interface, the longitudinal axis of the fastener is generally parallel to an axis of the bone.

17. The system of claim 15, wherein the first attachment interface and the second attachment interface are configured to allow for discrete rotational adjustments of the bone plate with respect to the intramedullary nail from among a plurality of different discrete rotational positions.

18. The system of claim 15, wherein the first attachment interface and the second attachment interface are configured to allow for an infinite number of rotational adjustment positions between the bone plate and the intramedullary nail.

19. The system of claim 15, wherein the first attachment interface comprises a proximal surface perpendicular to an axis of the bone.

20. The system of claim 15, the bone engagement surface is further securable to the exterior surface on either side of a fracture formed in the end portion of the bone, wherein:
the anterior bone engagement feature is securable to the exterior surface on a first side of the fracture that is formed in the end portion of the bone; and
the posterior bone engagement feature is securable to the exterior surface on a second side of the fracture that is formed in the end portion of the bone.

21. A system for repairing an end portion of a bone, the system comprising:
- an intramedullary nail comprising:
  - a first attachment interface formed on a superior surface of the intramedullary nail; and
- a bone plate comprising:
  - an arm comprising a bone engagement surface that is securable to an exterior surface of the end portion;
  - an anterior bone engagement feature protruding anteriorly of the arm;
  - a posterior bone engagement feature protruding posteriorly of the arm; and
  - a second attachment interface that is attachable to the first attachment interface of the intramedullary nail in order to couple the bone plate to the intramedullary nail;
- wherein:
  - the arm comprises a gooseneck shape that extends superiorly over the end portion and then distally toward the second attachment interface; and
  - the bone plate is sufficiently thin to allow the bone engagement surface to be flexed into conformity with the exterior surface.

22. The system of claim 21, the system further comprising a fastener comprising a longitudinal axis and configured to secure the second attachment interface to the first attachment interface at any of a plurality of relative orientations, wherein, with the second attachment interface secured to the first attachment interface, the longitudinal axis of the fastener is generally parallel to an axis of the bone.

23. The system of claim 21, wherein the first attachment interface comprises a proximal surface perpendicular to an axis of the bone.

* * * * *